United States Patent
Wondka

(10) Patent No.: US 7,588,033 B2
(45) Date of Patent: Sep. 15, 2009

(54) METHODS, SYSTEMS AND DEVICES FOR IMPROVING VENTILATION IN A LUNG AREA

(75) Inventor: Anthony David Wondka, Westlake Village, CA (US)

(73) Assignee: Breathe Technologies, Inc., San Ramon, CA (US)

( * ) Notice: Subject to any disclaimer, the term of this patent is extended or adjusted under 35 U.S.C. 154(b) by 236 days.

(21) Appl. No.: 10/870,849

(22) Filed: Jun. 17, 2004

(65) Prior Publication Data

US 2005/0005936 A1   Jan. 13, 2005

Related U.S. Application Data

(60) Provisional application No. 60/479,213, filed on Jun. 18, 2003.

(51) Int. Cl.
*A61M 15/00*   (2006.01)

(52) U.S. Cl. ............................. 128/207.14; 128/200.26

(58) Field of Classification Search ............ 128/200.26, 128/207.14, 207.15, 207.16; 604/516, 518, 604/514, 509, 48, 28, 35; 424/423; 607/99; 600/114, 116; 606/108
See application file for complete search history.

(56) References Cited

U.S. PATENT DOCUMENTS

| | | | |
|---|---|---|---|
| 3,267,935 | A | 8/1966 | Andreasen et al. |
| 3,357,427 | A | 12/1967 | Schreiber |
| 3,493,703 | A | 2/1970 | Finan |
| 3,610,247 | A | 10/1971 | Jackson |

(Continued)

FOREIGN PATENT DOCUMENTS

CA   2535450   2/2005

(Continued)

OTHER PUBLICATIONS

U.S. Appl. No. 12/153,423, filed May 19, 2008, Wondka et al.

(Continued)

*Primary Examiner*—Steven O Douglas
(74) *Attorney, Agent, or Firm*—Michele V. Frank; Patton Boggs LLP

(57) ABSTRACT

Methods, systems and devices are described for new modes of ventilation in which specific lung areas are ventilated with an indwelling trans-tracheobronchial catheter for the purpose of improving ventilation and reducing hyperinflation in that specific lung area, and for redistributing inspired air to other healthier lung areas, for treating respiratory disorders such as COPD, ARDS, SARS, CF, and TB. Trans-Tracheobronchial Segmental Ventilation (TTSV) is performed on either a naturally breathing or a mechanical ventilated patient by placing a uniquely configured indwelling catheter into a bronchus of a poorly ventilated specific lung area and providing direct ventilation to that area. The catheter can be left in place for extended periods without clinician attendance or vigilance. Ventilation includes delivery of respiratory gases, therapeutic gases or agents and evacuation of stagnant gases, mixed gases or waste fluids. Typically the catheter's distal tip is anchored without occluding the bronchus but optionally may intermittently or continuously occlude the bronchus. TTSV is optionally performed by insufflation only of the area, or by application of vacuum to the area, can include elevating or reducing the pressure in the targeted area to facilitate stagnant gas removal, or can include blocking the area to divert inspired gas to better functioning areas.

87 Claims, 12 Drawing Sheets

U.S. PATENT DOCUMENTS

| | | | |
|---|---|---|---|
| 3,721,233 A | 3/1973 | Montgomery et al. | |
| 3,741,208 A | 6/1973 | Jonsson et al. | |
| 3,794,026 A | 2/1974 | Jacobs | |
| 3,961,627 A | 6/1976 | Ernst et al. | |
| 3,991,790 A | 11/1976 | Russell | |
| 4,003,377 A | 1/1977 | Dahl | |
| 4,067,328 A | 1/1978 | Manley | |
| 4,231,365 A * | 11/1980 | Scarberry | 128/207.15 |
| 4,261,355 A | 4/1981 | Glazener | |
| 4,265,237 A | 5/1981 | Schwanbom et al. | |
| 4,274,162 A | 6/1981 | Joy et al. | |
| 4,413,514 A | 11/1983 | Bowman | |
| 4,449,523 A | 5/1984 | Szachowicz et al. | |
| 4,481,944 A | 11/1984 | Bunnell | |
| 4,488,548 A | 12/1984 | Agdanowski | |
| 4,506,667 A | 3/1985 | Ansite | |
| 4,527,557 A | 7/1985 | DeVries et al. | |
| 4,535,766 A | 8/1985 | Baum et al. | |
| 4,537,188 A | 8/1985 | Phuc | |
| 4,630,606 A | 12/1986 | Weerda et al. | |
| 4,644,947 A | 2/1987 | Whitwam et al. | |
| 4,744,356 A | 5/1988 | Greenwood | |
| 4,747,403 A | 5/1988 | Gluck et al. | |
| 4,773,411 A | 9/1988 | Downs | |
| 4,813,431 A | 3/1989 | Brown | |
| 4,825,859 A | 5/1989 | Lambert | |
| 4,832,014 A | 5/1989 | Perkins | |
| 4,838,255 A | 6/1989 | Lambert | |
| 4,850,350 A | 7/1989 | Jackson | |
| 4,865,586 A | 9/1989 | Hedberg | |
| 4,869,718 A | 9/1989 | Brader | |
| 4,905,688 A | 3/1990 | Vicenzi et al. | |
| 4,938,212 A | 7/1990 | Snook et al. | |
| 4,967,743 A | 11/1990 | Lambert | |
| 5,000,175 A | 3/1991 | Pue | |
| 5,002,050 A | 3/1991 | McGinnis | |
| 5,022,394 A * | 6/1991 | Chmielinski | 128/207.14 |
| 5,024,219 A | 6/1991 | Dietz | |
| 5,038,771 A | 8/1991 | Dietz | |
| 5,048,515 A | 9/1991 | Sanso | |
| 5,054,484 A | 10/1991 | Hebeler, Jr. | |
| 5,058,580 A * | 10/1991 | Hazard | 128/207.15 |
| 5,090,408 A | 2/1992 | Spofford et al. | |
| 5,101,820 A | 4/1992 | Christopher | |
| 5,127,400 A | 7/1992 | DeVries et al. | |
| 5,134,995 A | 8/1992 | Gruenke et al. | |
| 5,134,996 A | 8/1992 | Bell | |
| 5,148,802 A | 9/1992 | Sanders et al. | |
| 5,161,525 A | 11/1992 | Kimm et al. | |
| 5,181,509 A | 1/1993 | Spofford et al. | |
| 5,184,610 A | 2/1993 | Marten et al. | |
| 5,186,167 A | 2/1993 | Kolobow | |
| 5,193,533 A | 3/1993 | Body et al. | |
| 5,217,008 A | 6/1993 | Lindholm | |
| 5,233,979 A | 8/1993 | Strickland | |
| 5,239,994 A | 8/1993 | Atkins | |
| 5,243,972 A | 9/1993 | Huang | |
| 5,255,675 A | 10/1993 | Kolobow | |
| 5,258,027 A | 11/1993 | Berghaus | |
| 5,271,388 A | 12/1993 | Whitwam et al. | |
| 5,279,288 A | 1/1994 | Christopher | |
| 5,287,852 A | 2/1994 | Arkinstall et al. | |
| 5,303,700 A | 4/1994 | Weismann et al. | |
| 5,331,995 A | 7/1994 | Westfall et al. | |
| 5,339,809 A | 8/1994 | Beck, Jr. et al. | |
| 5,368,017 A | 11/1994 | Sorenson et al. | |
| 5,400,778 A | 3/1995 | Jonson et al. | |
| 5,419,314 A | 5/1995 | Christopher | |
| 5,438,980 A | 8/1995 | Phillips | |
| 5,460,613 A | 10/1995 | Ulrich et al. | |
| 5,474,062 A | 12/1995 | DeVires et al. | |
| 5,485,850 A | 1/1996 | Dietz | |
| 5,507,282 A | 4/1996 | Younes et al. | |
| 5,513,628 A | 5/1996 | Coles et al. | |
| 5,535,738 A | 7/1996 | Estes et al. | |
| 5,542,415 A | 8/1996 | Brody | |
| 5,546,935 A | 8/1996 | Champeau | |
| 5,549,106 A | 8/1996 | Gruenke et al. | |
| 5,558,086 A | 9/1996 | Smith et al. | |
| 5,598,840 A | 2/1997 | Iund et al. | |
| 5,669,380 A * | 9/1997 | Garry et al. | 128/207.14 |
| 5,687,714 A | 11/1997 | Kolobow et al. | |
| 5,690,097 A | 11/1997 | Howard et al. | |
| 5,715,812 A | 2/1998 | Deighan et al. | |
| 5,715,815 A * | 2/1998 | Lorenzen et al. | 128/207.14 |
| 5,720,278 A | 2/1998 | Lachmann et al. | |
| 5,735,268 A | 4/1998 | Chua et al. | |
| 5,740,796 A * | 4/1998 | Skog | 128/204.23 |
| 5,762,638 A | 6/1998 | Shikani et al. | |
| 5,791,337 A | 8/1998 | Coles et al. | |
| 5,819,723 A * | 10/1998 | Joseph | 128/207.14 |
| 5,865,173 A | 2/1999 | Froehlich | |
| 5,904,648 A | 5/1999 | Arndt et al. | |
| 5,906,204 A | 5/1999 | Beran et al. | |
| 5,911,756 A | 6/1999 | Debry | |
| 5,918,597 A | 7/1999 | Jones et al. | |
| 5,928,189 A | 7/1999 | Phillips et al. | |
| 5,931,162 A | 8/1999 | Christian | |
| 5,937,853 A | 8/1999 | Strom | |
| 5,954,050 A | 9/1999 | Christopher | |
| 5,964,223 A * | 10/1999 | Baran | 128/207.14 |
| 5,975,077 A | 11/1999 | Hofstetter et al. | |
| 5,975,081 A | 11/1999 | Hood et al. | |
| 6,039,696 A | 3/2000 | Bell | |
| 6,105,575 A | 8/2000 | Estes et al. | |
| 6,109,264 A | 8/2000 | Sauer | |
| 6,152,132 A * | 11/2000 | Psaros | 128/204.25 |
| 6,213,119 B1 | 4/2001 | Brydon et al. | |
| 6,220,244 B1 | 4/2001 | McLaughlin | |
| 6,227,200 B1 | 5/2001 | Crump et al. | |
| 6,305,374 B1 | 10/2001 | Zdrojkowski et al. | |
| 6,315,739 B1 | 11/2001 | Merilainen et al. | |
| 6,345,619 B1 | 2/2002 | Finn | |
| 6,357,438 B1 | 3/2002 | Hansen | |
| 6,378,520 B1 | 4/2002 | Davenport | |
| 6,427,690 B1 | 8/2002 | McCombs et al. | |
| 6,439,228 B1 | 8/2002 | Hete et al. | |
| 6,450,164 B1 | 9/2002 | Banner et al. | |
| 6,457,472 B1 | 10/2002 | Schwartz et al. | |
| 6,520,176 B1 | 2/2003 | Dubois et al. | |
| 6,520,183 B2 | 2/2003 | Amar | |
| 6,532,960 B1 | 3/2003 | Yurko | |
| 6,568,391 B1 | 5/2003 | Tatarek et al. | |
| 6,571,796 B2 | 6/2003 | Banner et al. | |
| 6,575,944 B1 | 6/2003 | McNary et al. | |
| 6,588,422 B1 | 7/2003 | Berthon-Jones et al. | |
| 6,609,517 B1 | 8/2003 | Estes et al. | |
| 6,626,175 B2 | 9/2003 | Jafari et al. | |
| 6,629,527 B1 | 10/2003 | Estes et al. | |
| 6,629,529 B2 | 10/2003 | Arnott | |
| 6,640,806 B2 | 11/2003 | Yurko | |
| 6,655,382 B1 | 12/2003 | Kolobow | |
| 6,666,208 B1 | 12/2003 | Schumacher et al. | |
| 6,668,829 B2 | 12/2003 | Biondi et al. | |
| 6,694,978 B1 | 2/2004 | Bennarsten | |
| 6,705,314 B1 | 3/2004 | O'Dea | |
| 6,722,360 B2 | 4/2004 | Doshi | |
| 6,722,362 B2 | 4/2004 | Hete et al. | |
| 6,752,151 B2 | 6/2004 | Hill | |
| 6,758,217 B1 | 7/2004 | Younes et al. | |
| 6,810,876 B2 | 11/2004 | Berthon-Jones | |
| 6,814,073 B2 | 11/2004 | Wickham | |
| 6,814,077 B1 | 11/2004 | Eistert | |
| 6,823,866 B2 | 11/2004 | Jafari et al. | |

| | | | | | | |
|---|---|---|---|---|---|---|
| 6,840,240 B1 | 1/2005 | Berthon-Jones et al. | | CA | 2652544 | 12/2007 |
| 6,854,462 B2 | 2/2005 | Berthon-Jones et al. | | CN | 2006-80043298.8 | 9/2006 |
| 6,877,511 B2 | 4/2005 | DeVries et al. | | CN | 200480029872 | 9/2006 |
| 6,910,480 B1 | 6/2005 | Berthon-Jones | | DE | 19626924 | 1/1998 |
| 6,910,482 B2 | 6/2005 | Bliss et al. | | DE | 10337138.9 | 3/2005 |
| 6,913,601 B2 * | 7/2005 | St. Goar et al. ............. 604/509 | | EP | 0125424 | 11/1984 |
| 6,915,803 B2 | 7/2005 | Berthon-Jones et al. | | EP | 0692273 | 1/1996 |
| 6,920,878 B2 | 7/2005 | Sinderby et al. | | EP | 0778035 | 6/1997 |
| 6,932,084 B2 | 8/2005 | Estes et al. | | EP | 1654023 | 5/2006 |
| 6,941,950 B2 * | 9/2005 | Wilson et al. .......... 128/207.14 | | EP | 1926517 | 6/2008 |
| 6,948,497 B2 | 9/2005 | Zdrojkowski et al. | | IN | 317/KOLNP/06 | 3/2008 |
| 6,951,217 B2 | 10/2005 | Berthon-Jones | | IN | 1105/KOLNP/2008 | 3/2008 |
| 6,971,382 B1 | 12/2005 | Corso | | JP | 2002-204830 | 7/2002 |
| 6,997,881 B2 | 2/2006 | Green et al. | | JP | 2006/522883 | 3/2009 |
| 7,000,612 B2 | 2/2006 | Jafari et al. | | JP | 2009-508645 | 3/2009 |
| 7,011,091 B2 | 3/2006 | Hill et al. | | WO | WO-98/01176 | 1/1998 |
| 7,017,574 B2 | 3/2006 | Biondi et al. | | WO | WO-0176655 | 10/2001 |
| 7,044,129 B1 | 5/2006 | Truschel et al. | | WO | WO-2005014091 | 2/2005 |
| 7,066,173 B2 | 6/2006 | Banner et al. | | WO | WO 2007/035804 | 3/2007 |
| 7,077,132 B2 | 7/2006 | Berthon-Jones | | WO | WO-2007035804 | 3/2007 |
| 7,080,646 B2 | 7/2006 | Wiesmann et al. | | WO | WO-2007142812 | 12/2007 |
| 7,100,607 B2 | 9/2006 | Zdrojkowski et al. | | WO | WO 2008/019102 | 2/2008 |
| 7,121,277 B2 | 10/2006 | Ström | | | | |
| 7,152,598 B2 | 12/2006 | Morris et al. | | | | |
| 7,156,090 B2 | 1/2007 | Nomori | | | | |
| 7,195,016 B2 | 3/2007 | Loyd et al. | | | | |
| 7,222,623 B2 | 5/2007 | DeVries et al. | | | | |
| 7,255,103 B2 | 8/2007 | Bassin | | | | |
| 7,267,122 B2 | 9/2007 | Hill | | | | |
| 7,270,128 B2 | 9/2007 | Berthon-Jones et al. | | | | |
| 7,296,573 B2 | 11/2007 | Estes et al. | | | | |
| 7,373,939 B1 | 5/2008 | DuBois et al. | | | | |
| 2001/0035185 A1 | 11/2001 | Christopher | | | | |
| 2002/0179090 A1 | 12/2002 | Boussignac | | | | |
| 2003/0121519 A1 | 7/2003 | Estes et al. | | | | |
| 2003/0145853 A1 | 8/2003 | Muellner | | | | |
| 2003/0145856 A1 | 8/2003 | Zdrojkowski et al. | | | | |
| 2003/0150455 A1 | 8/2003 | Bliss et al. | | | | |
| 2004/0040560 A1 | 3/2004 | Euliano et al. | | | | |
| 2004/0221848 A1 | 11/2004 | Hill | | | | |
| 2004/0221854 A1 | 11/2004 | Hete et al. | | | | |
| 2004/0231674 A1 | 11/2004 | Tanaka | | | | |
| 2004/0237963 A1 | 12/2004 | Berthon-Jones | | | | |
| 2004/0255943 A1 | 12/2004 | Morris et al. | | | | |
| 2005/0005936 A1 | 1/2005 | Wondka | | | | |
| 2005/0005938 A1 | 1/2005 | Berthon-Jones et al. | | | | |
| 2005/0034721 A1 | 2/2005 | Freitag | | | | |
| 2005/0034724 A1 | 2/2005 | O'Dea | | | | |
| 2005/0061322 A1 | 3/2005 | Freitag | | | | |
| 2005/0087190 A1 | 4/2005 | Jafari et al. | | | | |
| 2005/0098179 A1 | 5/2005 | Burton et al. | | | | |
| 2005/0121033 A1 | 6/2005 | Starr et al. | | | | |
| 2005/0121038 A1 | 6/2005 | Christopher | | | | |
| 2005/0166924 A1 | 8/2005 | Thomas et al. | | | | |
| 2005/0247308 A1 | 11/2005 | Frye et al. | | | | |
| 2006/0005834 A1 | 1/2006 | Aylsworth et al. | | | | |
| 2006/0096596 A1 | 5/2006 | Occhialini et al. | | | | |
| 2006/0124134 A1 | 6/2006 | Wood | | | | |
| 2006/0149144 A1 | 7/2006 | Lynn et al. | | | | |
| 2006/0150972 A1 | 7/2006 | Mizuta et al. | | | | |
| 2006/0201504 A1 | 9/2006 | Singhal et al. | | | | |
| 2006/0243278 A1 | 11/2006 | Hamilton et al. | | | | |
| 2007/0125379 A1 | 6/2007 | Pierro et al. | | | | |
| 2007/0181125 A1 | 8/2007 | Mulier | | | | |
| 2008/0011298 A1 | 1/2008 | Mazar et al. | | | | |
| 2008/0029088 A1 | 2/2008 | Freitag | | | | |
| 2008/0041371 A1 | 2/2008 | Freitag | | | | |
| 2008/0135044 A1 | 6/2008 | Freitag et al. | | | | |
| 2009/0107494 A1 | 4/2009 | Freitag et al. | | | | |

FOREIGN PATENT DOCUMENTS

| | | |
|---|---|---|
| CA | 2623756 | 3/2007 |

OTHER PUBLICATIONS

International Search Report and Written Opinion for PCT/US08/78033, issued Dec. 3, 2008.

International Search Report and Written Opinion for PCT/US08/78031, issued Nov. 24, 2008.

Christopher, et al., "Transtracheal Oxygen Therapy for Refractory Hypoxemia," *JAMA*, 1986, vol. 256, No. 4, pp. 494-497.

Fink, J.B., "Helium-Oxygen: An Old Therapy Creates New Interest," *J Resp Care Pract now RT for Decision Makers in Respiratory Care*, Apr. 1999, pp. 71-76.

Haenel, et al., "Efficacy of Selective Intrabronchial Air Insufflation in Acute Lobar Colapse," *Am J Surg*, 1992, vol. 164, No. 5, pp. 501-505.

"AARC Clinical Practice Guideline: Oxygen Therapy in the Home or Extended Care Facility," *Respir Care*, 1992, vol. 37, No. 8, pp. 918-922.

MacIntyre, N. R., "Long-Term Oxygen Therapy: Conference Summary," *Resp Care*, 2000, vol. 45, No. 2, pp. 237-245.

*VHA/DOD Clinical Practice Guideline*, "Management of Chronic Obstructive Pulmonary Disease," Ver. 1.1a, Aug. 1999, Updated Nov. 1999.

Blanch, L. L., "Clinical Studies of Tracheal Gas Insufflation," *Respir Care*, 2001, vol. 46, No. 2, pp. 158-166.

Gregoretti, et al., "Transtracheal Open Ventilation in Acute Respiratory Failure Secondary to Severe Chronic Obstructive Pulmonary Disease Exacerbation," *Am J Respir Crit Care Med*, 2006, vol. 173, No. 8, pp. 877-881.

Christopher, et al., "Preliminary Observations of Transtracheal Augmented Ventilation for Chronic Severe Respiratory Disease," *Respir Care*, 2001, vol. 46, No. 1, pp. 15-25.

Chang, et al., "Reduced Inspiratory Muscle endurance Following Successful Weaning From Prolonged Mechanical Ventilation," *Chest*, 2005, vol. 128, No. 2, pp. 553-559.

Gaughan, et al., "A Comparison in a Lung Model of Low- and High-Flow Regulators for Transtracheal Jet Ventilation," *Anesthesiology*, 1992, vol. 77, No. 1, pp. 189-199.

Menon, et al., "Tracheal Perforation. A Complication Associated with Transtracheal Oxygen Therapy," *Chest*, 1993, vol. 104, No. 2, pp. 636-637.

Rothe, et al., "Near Fatal Complication of Transtracheal Oxygen Therapy with the SCOOP(R) System," *Pneumologie*, 1996, vol. 50, No. 10, pp. 700-702. (English Abstract provided).

International Search Report and Opinion for Application No. PCT/US07/17400, dated Apr. 28, 2008.

Ambrosino, "Weaning and Respiratory Muscle Dysfunction: The Egg Chicken Dilemma," Chest, 2005, vol. 128(2), pp. 481-483.

Messinger et al., "Using Tracheal Pressure to Trigger the Ventilator and Control Airway Pressure During Continuous Positive Airway Pressure Decreases Work of Breathing," Chest, 1995, vol. 108, No. 2, pp. 509-514.

Messinger et al., "Tracheal pressure triggering a demand flow CPAP system decreases work of breathing," Anesthesiology, 1994, vol. 81, A272.
Koska et al., "Evaluation of a fiberoptic system for airway pressure monitoring," J. Clin Monit, 1993, vol. 10, No. 4, pp. 247-250.
Banner et al., "Imposed work of breathing and methods of triggering demand-flow, continuous positive airway pressure system," Critical Care Medicine, 1993, vol. 21, No. 2, pp. 183-190.
Banner et al., "Site of pressure measurement during spontaneous breathing with continuous positive airway pressure: Effect on calculating imposed work of breathing," Critical Care, 1992, vol. 20, No. 4, pp. 528-533.
Sinderby et al., "Neural control of mechanical ventilation in respiratory failure", Nat Med., 1999; 5:1433-1436.
Tiep et al., "Pulsed nasal and transtracheal oxygen delivery," *Chest*, 1990, vol. 97, pp. 364-368.
Yaegar et al., "Oxygen Therapy Using Pulse and Continuous Flow With a Transtracheal Catheter and a Nasal Cannula," *Chest*, 1994, vol. 106, pp. 854-860.
Passy-Muir Inc., "Clinical Inservice Outline", Aug. 1997, revised Apr. 2004, 19 pages.
Charlotte Regional Medical Center, "Application of the Passy-Muir Tracheostomy and Ventilator", Speech-Language Pathology Department, Jan. 1995, 8 pages.
"Passy-Muir Speaking Valves," Speech Pathology Department, Nov. 13, 1998, revised May 29, 2002, 7 pages.
Prigent et al., "Comparative Effects of Two Ventilatory Modes on Speech in Tracheostomized Patients with Neuromuscular Disease," *Am J Respir Crit Care Med*, 2003, vol. 167, No. 8, pp. 114-119.
International Search Report and Written Opinion for PCT/US07/12108, issued Aug. 8, 2008.
U.S. Appl. No. 11/523,519, filed Sep. 20, 2006, Freitag.
U.S. Appl. No. 10/567,746, filed Sep. 10, 2007, Freitag.
U.S. Appl. No. 11/523,518, filed Sep. 20, 2006, Freitag et al.
U.S. Appl. No. 60/960,392, filed Sep. 26, 2007, Wondka et al.
U.S. Appl. No. 60/294,514, filed May 18, 2007, Wondka et al.
U.S. Appl. No. 60/960,370, filed Sep. 26, 2007, Wondka et al.
U.S. Appl. No. 10/771,803, filed Feb. 17, 2005, Lutz Freitag.
U.S. Appl. No. 11/798,965, filed May 18, 2007, Lutz Freitag.
International Search Report for WO 2005/014091 (Application No. PCT/DE04/1646), filed Jan. 17, 2005.
European Search Report issued Oct. 19, 2007 in co-pending EP 04762494.
Co-pending U.S. Appl. No. 11/882,530, filed Aug. 30, 2007, Lutz Freitag.
U.S. Appl. No. 60/479,213, Jun. 16, 2003, Wondka.
U.S. Appl. No. 60/718,318, Sep. 20, 2005, Freitag et al.
U.S. Appl. No. 60/801,104, May 18, 2006, Freitag.
U.S. Appl. No. 60/835,066, Aug. 3, 2006, Freitag et al.
U.S. Appl. No. 60/924,514, May 18, 2007, Wondka et al.
U.S. Appl. No. 60/960,362, Sep. 26, 2007, Wondka et al.
U.S. Appl. No. 60/960,370, Sep. 26, 2007, Wondka et al.
U.S. Appl. No. 61/071,251, Apr. 18, 2008, Wondka et al.
U.S. Appl. No. 61/071,252, Apr. 18, 2008, Wondka et al.
Co-pending U.S. Appl. No. 61/091,198, Aug. 22, 2008, Allum et al.
Co-pending U.S. Appl. No. 61/101,826, Oct. 1, 2008, Wondka et al.
Co-pending U.S. Appl. No. 61/136,269, Aug. 22, 2008, Allum et al.
Co-pending U.S. Appl. No. 61/166,150, Apr. 2, 2009, Allum et al.
In the U.S. Patent and Trademark Office, Office Action in re: U.S. Appl. No. 10/771,803, dated Jun. 14, 2007, 17 pages.
In the U.S. Patent and Trademark Office, Office Action in re: U.S. Appl. No. 11/523,519, dated Mar. 7, 2007, 12 pages.
In the U.S. Patent and Trademark Office, Final Office Action in re: U.S. Appl. No. 11/523,519, dated Nov. 26, 2007, 21 pages.
In the U.S. Patent and Trademark Office, Final Office Action in re: Application No. 11/523,519, dated Jul. 11, 2008, 24 pages.
In the U.S. Patent and Trademark Office, Office Action in re: U.S. Appl. No. 11/798,965, dated Jul. 29, 2008, 22 pages.
In the U.S. Patent and Trademark Office, Final Office Action in re: Appl. No. 11/798,965, dated Apr. 9, 2009, 9 pages.
CN 2007-80022806.9, Dec. 18, 2008, Freitag et al., Previously submitted WO 2007/142812 is the English Language equivalent.
EP 2023987 (co-pending), Feb. 18, 2009, Freitag, Previously submitted WO 2007/142812 is the English Language equivalent.
IN 6979/Chen/2008 (co-pending), Dec. 18, 2008, Freitag et al., Previously submitted WO 2007/142812 is the English Language equivalent.
JP 2009-511111 (co-pending), May 18, 2007, Freitag et al., Previously submitted WO 2007/142812 is the English Language equivalent.
EP 07836502.0 (co-pending), Feb. 14, 2008, Freitag et al., Previously submitted WO 2008/019102 is the English Language equivalent.
National Phase of PCT/US07/017400 in Japan (co-pending), Feb. 14, 2008, Freitag et al., Previously submitted WO 2008/019102 is the English Language equivalent.
National Phase of PCT/US07/017400 in India (co-pending), Feb. 14, 2008, Freitag et al., Previously submitted WO 2008/019102 is the English Language equivalent.
WO 2008/144589 (co-pending), Nov. 27, 2008, Breathe Technologies, Inc.
WO 2008/144669 (co-pending), Nov. 27, 2008, Breathe Technologies, Inc.
WO 2009/042974 (co-pending), Apr. 2, 2009, Breathe Technologies, Inc.
WO 2009/042973 (co-pending), Apr. 2, 2009, Breathe Technologies, Inc.
PCT/US2009/041027 (co-pending), Apr. 17, 2009, Breathe Technologies, Inc.
PCT/US2009/041034 (co-pending), Apr. 17, 2009, Breathe Technologies, Inc.
DE 10 2006 023 637 (co-pending), Nov. 22, 2007, Breathe Technologies, Inc., Abstract.
International Search Report and Written Opinion for PCT/US08/64015, issued Sep. 26, 2008. (co-pending).
International Search Report and Written Opinion for PCT/US08/64164, issued Sep. 29, 2008. (co-pending).
International Preliminary Report on Patentability for PCT/US2007/012108, issued Nov. 18, 2008. (co-pending).

* cited by examiner

FIGURE 1
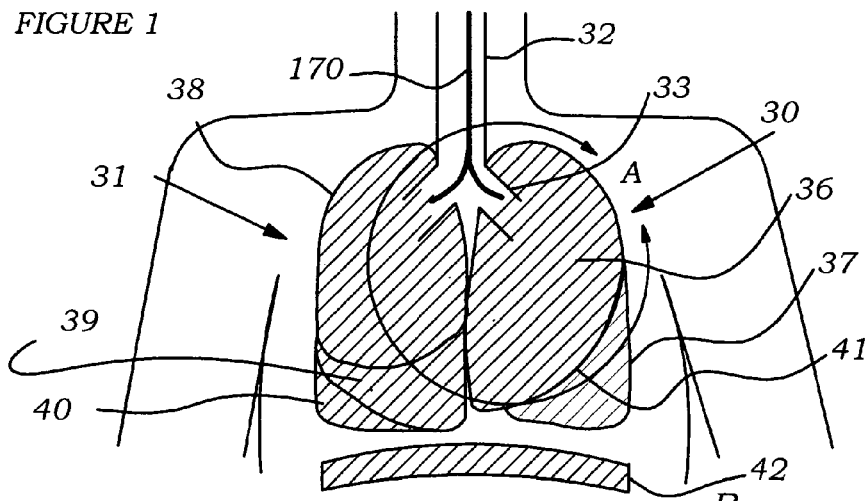
FIG. 1B DETAIL B
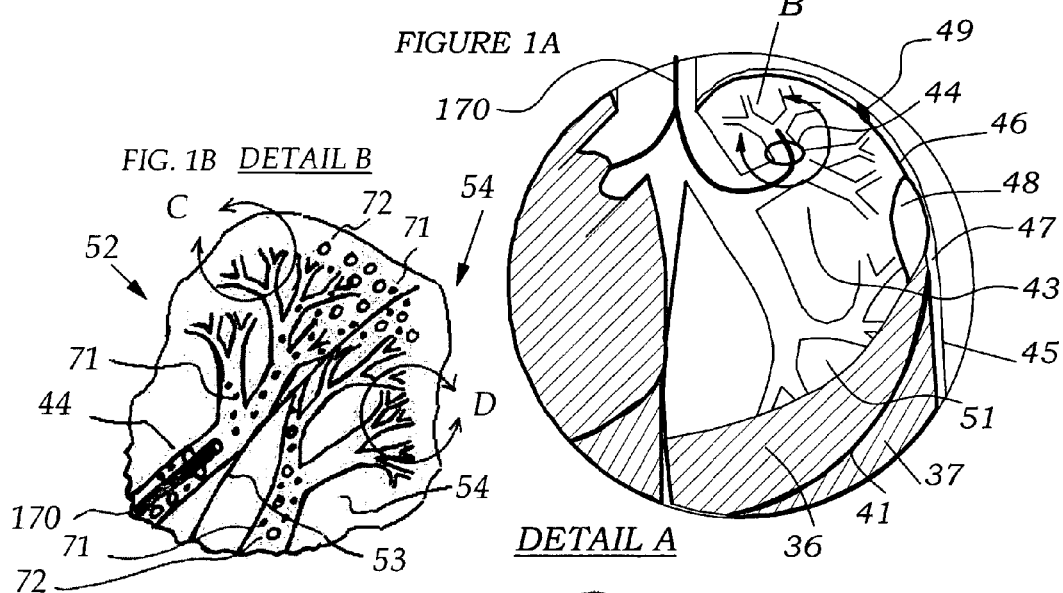
FIGURE 1A
DETAIL A
FIG. 1C DETAIL C
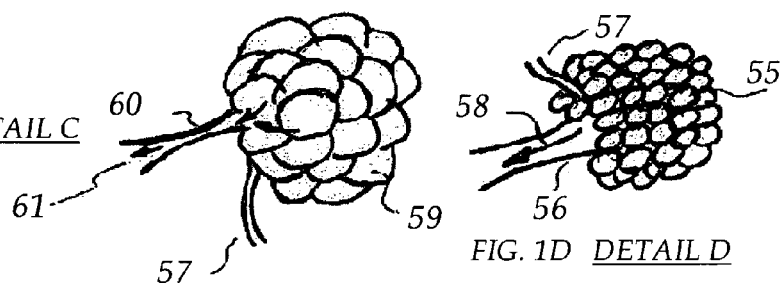
FIG. 1D DETAIL D

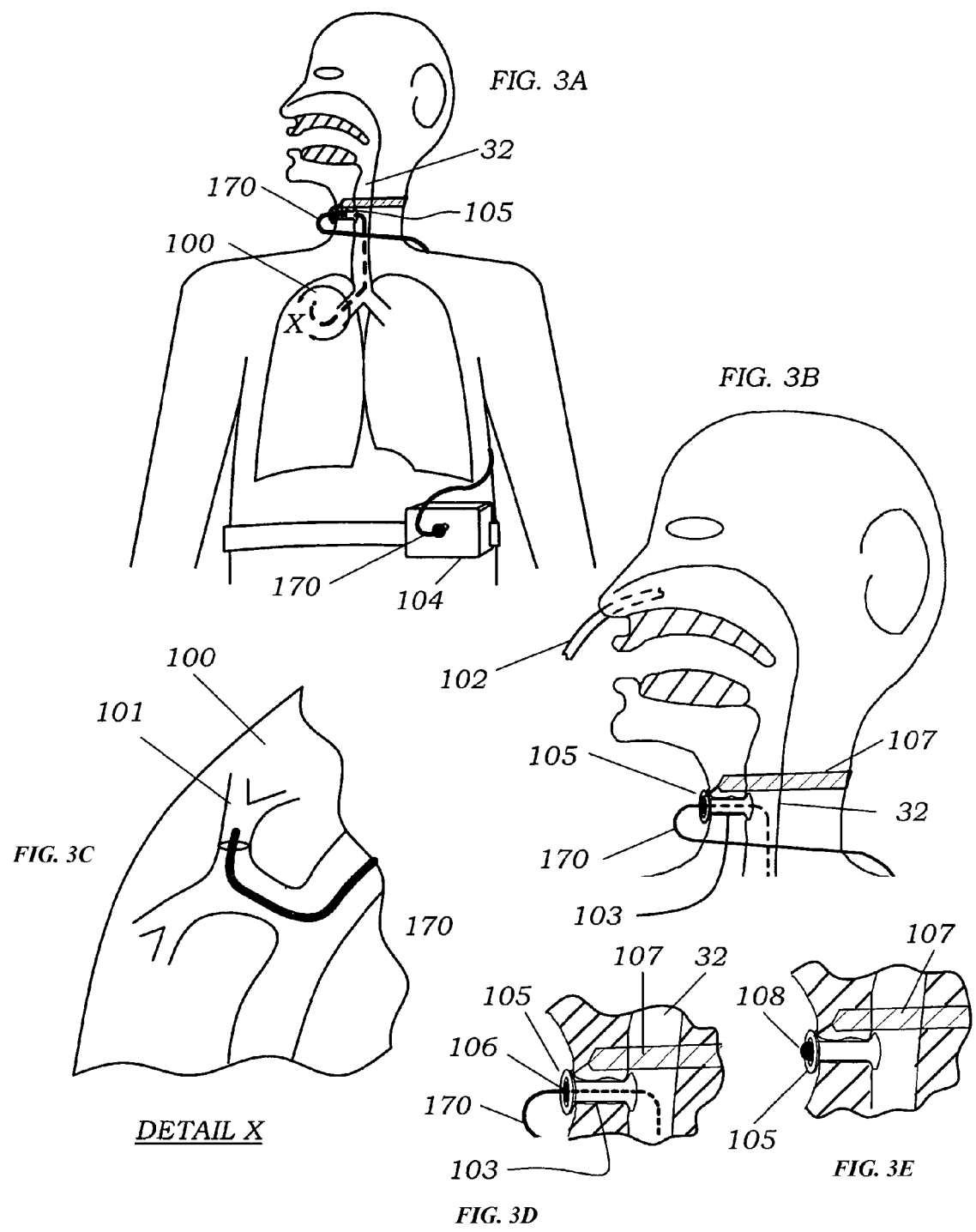

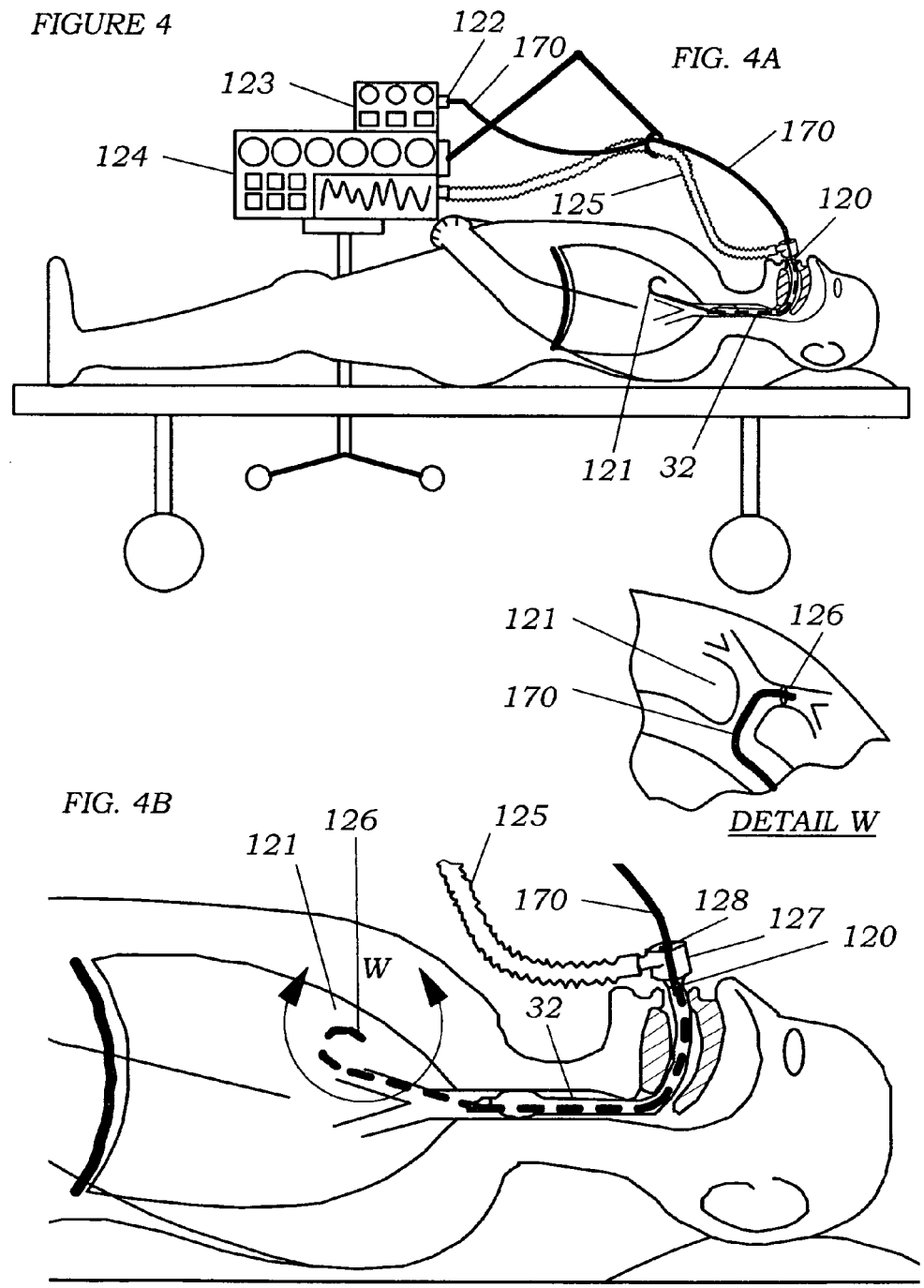

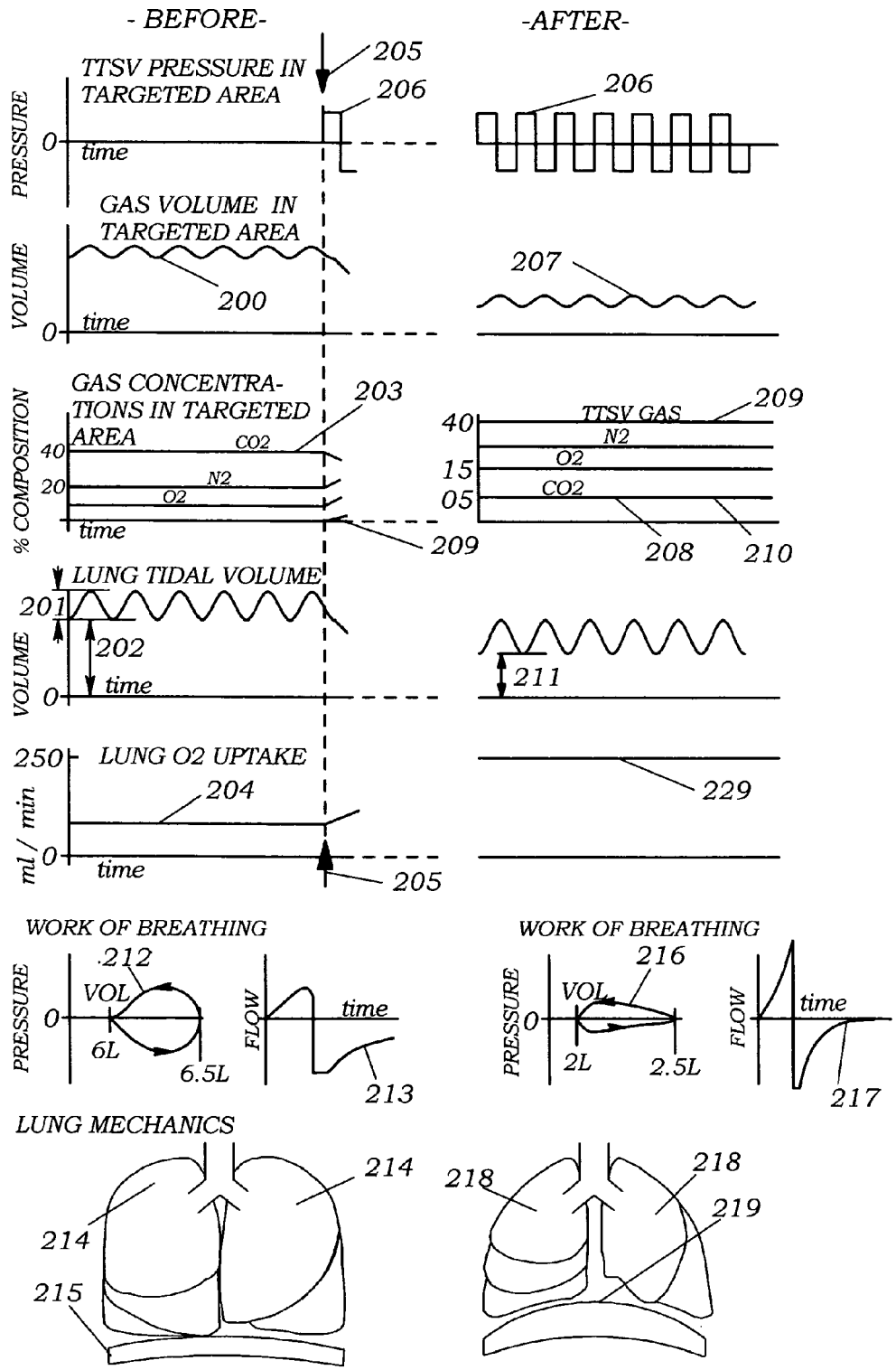

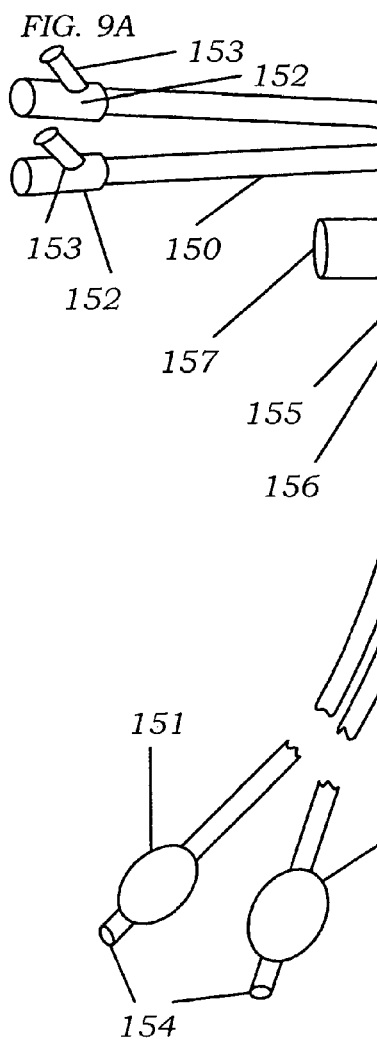
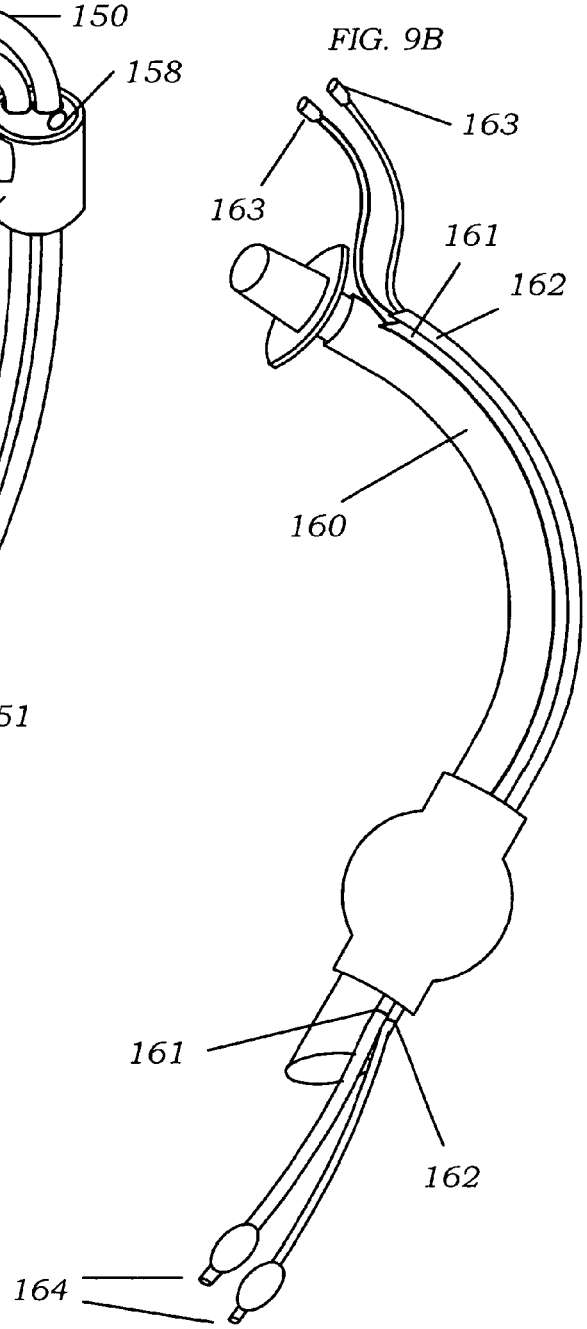
FIG. 9A
FIG. 9B

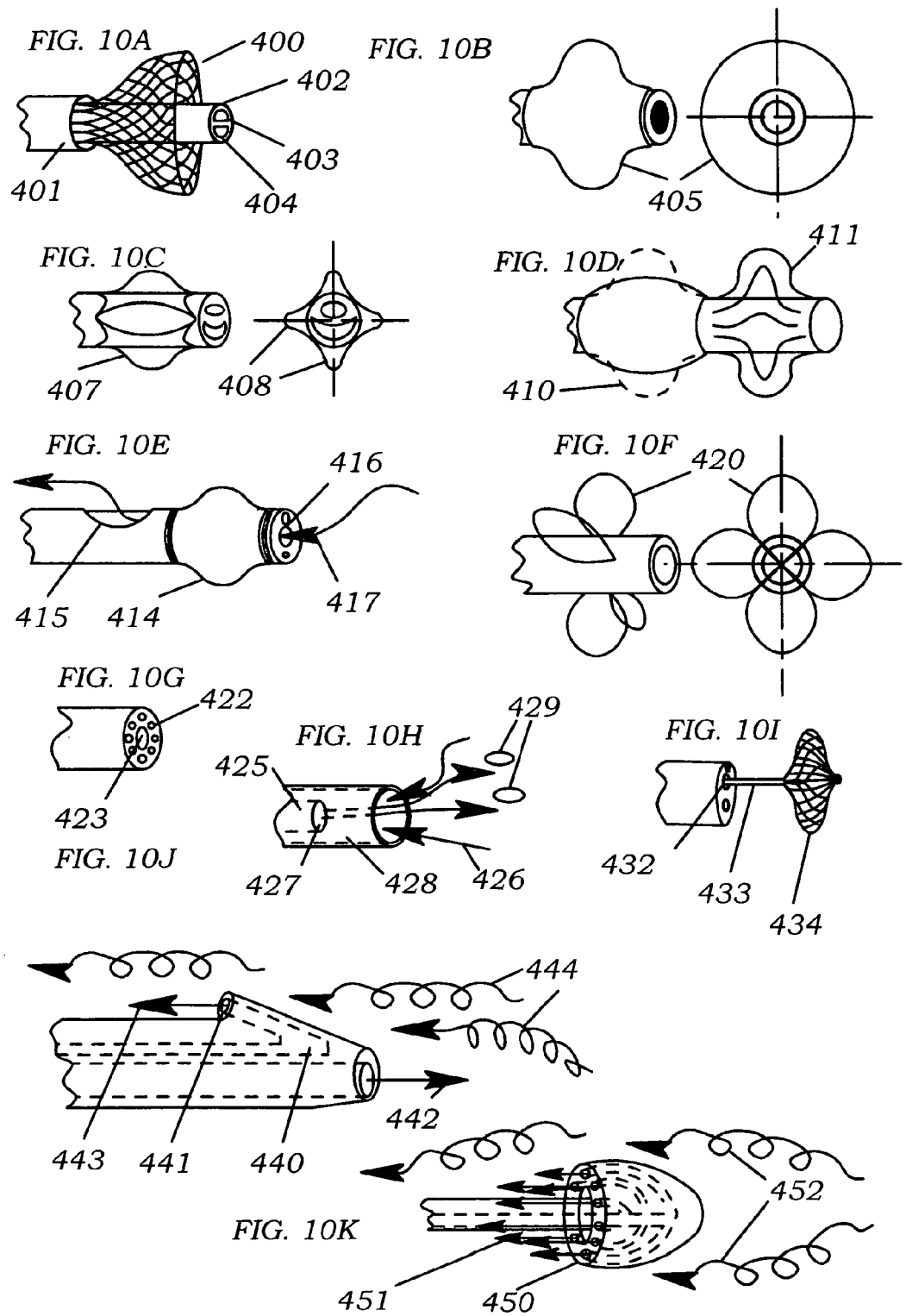

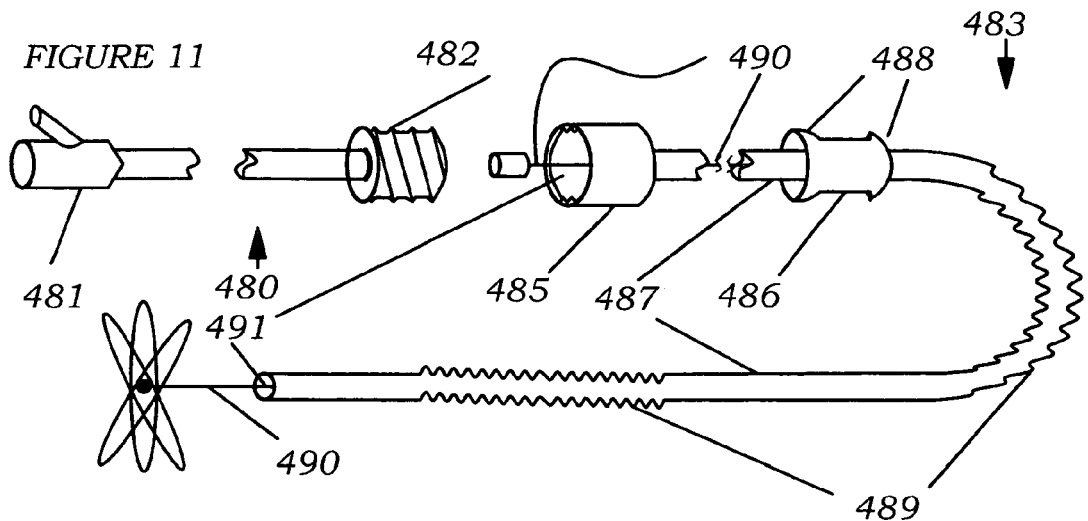
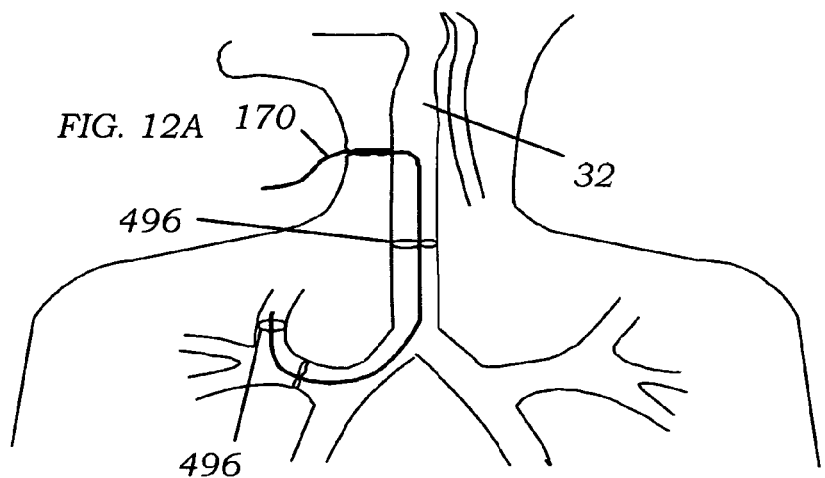
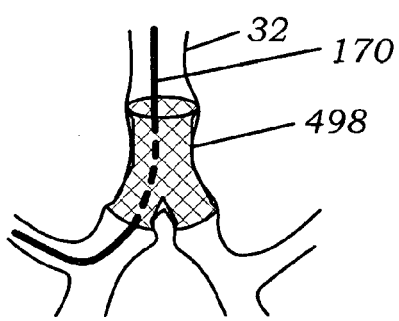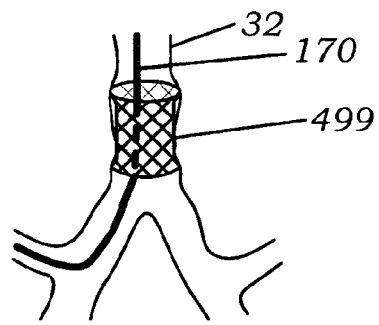

METHODS, SYSTEMS AND DEVICES FOR IMPROVING VENTILATION IN A LUNG AREA

CROSS REFERENCE TO RELATED APPLICATIONS

This application claims Provisional Patent Application No. 60/479,213 as a predicate application with the respective priority filing date of Jun. 18, 2003.

STATEMENT REGARDING FEDERALLY SPONSORED RESEARCH OR DEVELOPMENT

Not Applicable

DESCRIPTION OF ATTACHED APPENDIX

Not Applicable

GOVERNMENT INVENTION OR CONTRACT WITH GOVERNMENT

None

ENTITY

Small Entity Concern

PRIOR ART

U.S. Pat. Nos. 4,825,859; 4,838,255; 4,850,350; 4,967,743; 5,000,175; 5,134,996; 5,186,167; 5,193,533; 5,255,675; 5,460,613; 5,513,628; 5,598,840; 5,791,337; 5,904,648; 6,227,200; 6,520,183; 6,575,944; 6,575,944; U.S. Published Patent Applications: 20010035185; 20020179090.

OTHER RELATED APPLICATIONS

Fink J. B.; *Helium-oxygen: An Old Therapy Creates New Interest.* (J Resp Care Pract April 1999; 71-76)

Christopher K L et al.; *Transtracheal oxygen for refractory hypoxemia.* (JAMA 1986; 256: 494-7)

Gaebek J. B. et al; *Efficacy of Selective Intrabronchial Air Insufflation in Acute Lobar Collapse.* (Am J of Sur 1992; 164:501-505)

AARC Clinical Practice Guideline: *Oxygen Therapy in the Home or Extended Care Facility* (Respir Care 1992; 37:918-922)

MacIntyre, Neil; *Long-term Oxygen Therapy: Conference Summary* (Respir Care 2000; 45(2):237-245) VHA/DOD Clinical Proactice Guideline for the Management of Chronic Obstructive Pulmonary Disease (VHA 1999 August 116)

Blanch, L; *Clinical Studies of Tracheal Gas Insufflation* (Respir Care 2001 ; 46(2):158-166)

BACKGROUND OF THE INVENTION

The present invention relates to the field of respiratory therapy and specifically to the field of lung ventilation to treat a variety of pulmonary diseases.

Lung diseases are the number one category of diseases and a leading cause of death worldwide. Some lung diseases, such as Chronic Obstructive Pulmonary Disease (COPD), Acute Respiratory Distress Syndrome (ARDS), Severe Acute Respiratory Syndrome (SARS) and cystic fibrosis (CF) usually require some form of ventilation assistance or delivery of therapeutic agents in order to clinically improve the patient.

COPD in particular effects tens of millions of people and is one of the top five leading causes of death. COPD is a spectrum of problems, including bronchitis and emphysema, and involves airway obstruction, lung elasticity loss and trapping of stagnant $CO_2$-rich air in the lung. Emphysema, the worst form of COPD, occurs when there is a breakdown in the elasticity in the lung changing clusters of individual alveoli into large air pockets, thereby significantly reducing the surface area for gas transfer. In some cases air leaks out of the compromised walls of the minute airways to the periphery of the lung causing the membranous lining to separate and forming large air vesicles called bullae. Also due to elasticity loss, small conducting airways leading to the alveoli become flaccid and have a tendency to collapse during exhalation, trapping large volumes of air in the now enlarged air pockets, thus reducing bulk air flow exchange and causing $CO_2$ retention in the trapped air. Mechanically, because of the large amount of trapped air at the end of exhalation, known as elevated residual volume, the intercostal and diaphragmatic inspiratory muscles are forced into a pre-loaded condition, reducing their leverage at the onset of an inspiratory effort thus increasing work-of-breathing and dyspnea. Also, areas with more advanced emphysema and more trapped air tend to comprise the majority of the chest cavity volume and tend to fill preferentially during inspiration due to their low elasticity, thus causing the healthier portions to be disproportionately compressed rather than inflating normally during inspiration and receiving their share of inspired air. In emphysema therefore more effort is expended to inspire less air and the air that is inspired contributes less to gas exchange.

ARDS is a respiratory insufficiency caused by a variety of underlying problems such as lung injury, infection, edema, or atelectasis. SARS is a sudden respiratory insufficiency and appears to be caused by a viral infection. CF is a genetic condition in which airways secrete copious amounts of mucus and are inflamed.

Conventionally prescribed therapies for COPD and ARDS and sometimes SARS and CF include pharmacological agents (beta-agonists, aerosolized bronchodilators, anti-inflammatories and mucolytics), supplemental long term oxygen therapy (LTOT) delivered nasally or via tracheotomy, BiLevel Continuous Positive Airway Pressure (BiPAP), which lowers work of inspiration by providing a steady stream of pressure, Tracheal Oxygen Gas Insufflation (TGI), described by Christopher, *JAMA* 1986; 256: 494-7, which reduces $CO_2$ content in the upper airways thus allowing higher $O_2$ concentrations to reach the distal airways, respiratory muscle rehabilitation, pulmonary hygiene, such as lavage and percussion therapy, lung volume reduction surgery (LVRS) and lung transplantation (LX). These therapies all have certain disadvantages and limitations with regard to effectiveness, targeting accuracy, risk or availability. Usually, after progressive decline in lung function despite attempts at therapy, patients become physically incapacitated or sometimes require more invasive mechanical ventilation to survive in which case weaning from ventilator dependency is often times difficult. Conventional invasive ventilation modes include Continuous Mechanical Ventilation (CMV), Synchronized Intermittent Mechanical Ventilation (SIMV), Positive End Expiratory Pressure (PEEP) therapy, and high frequency jet ventilation (HFJV).

Some newer ventilatory methods have been studied in the attempt to improve treatment of COPD and ARDS. One such method described by Fink, *J Resp Care Pract* April 1999; 71 is ventilation of a lung with gases of low molecular weights and low viscosity, such as helium-oxygen mixtures or nitric oxide, in order to decrease gas flow resistance and lower surface tension in distal airways and alveolar surfaces, thus increasing oxygen transfer across the alveolar surface into the blood. Another new method includes liquid perfluorocarbon ventilation which can displace mucus in distal airways while still conducting oxygen thus improving gas flow. Another method never successfully commercialized is Negative End Expiratory Pressure (NEEP), which helps remove CO2-rich gas during the exhalation cycle. These invasive methods typically ventilate COPD and ARDS patients more effectively then conventional invasive ventilation modes and may improve weaning, but they are significantly limited in efficacy because they can not easily be provided as chronic treatments and are not target specific. Rather they are inherently designed to treat the whole lung from the upper airway and hence do not address the significant problem of hyperinflation and areas of trapped stagnant gas, nor the problem of maldistribution of inspiratory gas volume.

Some additional devices and techniques have been invented with the aim of improving efficacy. U.S. Pat. No. 6,575,944 describes a catheter that is used for medication delivery through an endotracheal tube. That invention is good for pharmacological therapy on a mechanically ventilated patient, however the invention does not address the significant ventilation needs of the diseased lungs such as trapped gas and hyperinflated lungs.

U.S. Pat. No. 6,520,183 describes a catheter used to block on lung and delivery anesthesia to the other lung. That invention and other like it can only be used for one lung ventilation, almost always for surgery. That invention can be used in the unintended use of shunting ventilation to one lung, if the other lung is too diseased, however this usage would have significant limitations in that lobar or segmental sections of lung could not be individually blocked; hence this therapy would not be selective at all.

U.S. Pat. Nos. 6,227,200; 5,791,337; 5,598,840; 5,513,628; 5,460,613; 5,134,996; and 4,850,350 all describe catheters used for intermittently accessing and suctioning the trachea and main stem bronchi during through a tracheal tube during mechanical ventilation. That invention does not address the severe ventilation problems of the diseased lung, such as trapped air, hyperinflation, and poor airflow and perfusion distribution.

U.S. Pat. No. 5,904,648 describes a catheter for blocking airflow to one lung in order to ventilate and deliver anesthesia to the other side while the blocked side is being operated on. Again, that invention does not address improving ventilation and gas exchange.

U.S. Pat. Nos. 5,255,675 and 5,186,167 describe a catheter placed in the trachea through which the trachea is insufflated with oxygen. In clinical practice that invention and others like it have been proven to reduce the amount of CO2 in the lung and thus improve ventilation, however because the therapy described in this invention can inherently only be applied to the upper airways, it does nothing to improve the significant hyperinflation, air trapping and airflow and perfusion maldistribution of diseased lungs, and thus the therapy is severely limited. Indeed this therapy has not been well received clinically because the amount of benefit does not justify the added attention required.

U.S. Pat. No. 5,193,533 describes an invention similar to U.S. Pat. No. 5,255,675 in which high frequency ventilation is administered to the trachea to improve oxygenation. That invention has been proven clinically useful during short term medical procedures because the lung can be effectively mechanically ventilated at lower pressures but it is not useful as a subacute or chronic therapy as it does not reduce the air trapping, hyperinflation, or airflow and blood perfusion maldistribution.

U.S. Pat. Nos. 4,967,743; 4,838,255 and 4,825,859 describe a catheter for suctioning and ravaging the airways. That invention is limited to managing the airway integrity and pulmonary hygiene and is not suited for directly improving the underlying causes of air trapping, hyperventilation, and air flow maldistribution in the lung.

U.S. Patent Application 20020179090 describes an aspiration catheter for removing phlegm from a lung. This invention is only useful in airway management and is not suited for directly improving the underlying causes of air trapping, hyperventilation, and air flow maldistribution in the lung.

U.S. Patent Application 20010035185 describes a nasal-pharyngeal catheter for delivering breathing gases to the pharynx to supplement regular ventilation or breathing. That invention is incrementally more effective than LTOT in that the gases are delivered more effectively but unfortunately the technique can not directly improve the underlying causes of air trapping, hyperventilation, and air flow maldistribution in the lung It must be emphasized that an effective ventilation treatment should ideally target specific areas of the lung that are most diseased yet all the methods described in the prior art employ ventilation on the entire lung as a whole, rather than on targeted lung areas that are more diseased. Therefore, all known ventilation modes allow trapped CO2 to persist in the worst effected areas of the lung and allow these areas to remain hyperinflated with the CO2-rich air, thus taking up valuable space in the chest cavity and compressing other potentially contributory lung areas. Other inventions or conventional therapies are either to traumatic, too transient, not site-specific, too experimental or not effective. The present invention disclosed herein addresses these shortcomings as will become apparent in the later descriptions.

BRIEF SUMMARY OF THE INVENTION

The present invention disclosed herein takes into consideration the problems and challenges not solved by the aforementioned prior art methods. In summary, this invention accomplishes (1) effective and direct cannulation of the lung area requiring treatment for a targeted site-specific treatment, (2) provides the option of sub-chronic or chronic treatment without the vigilance of a clinician, either in the hospital setting or in the home-care setting, and can be titrated accordingly, (3) is atraumatic, (4) improves hyperinflation and stagnant gas trapping in the distal spaces, (5) improves the maldistribution of airflow and blood perfusion, and (5) is cost effective.

The present invention provides a method for directly ventilating an area in a lung to improve the gas exchange in that area, typically for the treatment of COPD, although other respiratory diseases, such as ARDS, SARS, CF and TB may also benefit from this approach. The method, Trans-Tracheobronchial Segmental Ventilation (TTSV), is performed by (a) catheterizing the lung area with an indwelling catheter that can be left in place for extended periods without the vigilance of a clinician, and (b) ventilating the lung area via the catheter by delivering a ventilation gas and/or therapeutic substance such as a gas, liquid, solid or plasma, during an insufflation phase and removing waste and mixed gases from the area during an exhaust phase. The scientific principles employed to accomplish TTSV are fluid dynamics, the physical laws of mass transfer, i.e., gas and tissue diffusivity, gas concentration gradients and pressure gradients, as well as the physical laws of collapsible tubes and hemoglobin biochemistry laws.

In a preferred embodiment of the present invention the feeding bronchus of the targeted lung area is catheterized with an indwelling catheter anchored in the bronchus such that it can remain in place for extended periods without being attended by a person. The catheter enters the bronchial tree from the upper airway, either through an artificial airway such as a tracheal tube or through a natural airway such as the nasal passage or through a percutaneous incision such as a cricothyrotomy and is advanced to the targeted LUNG AREA through the bronchial tree with endoscopic or fluoroscopic guidance, where the tip is anchored in the airway. For ventilation and hygiene considerations, the catheter entry point into the body typically includes a self-sealing and tensioning connector that controls fluid from escaping from around the catheter shaft, but which permits the catheter to slide axially to compensate for patient movement or for elective catheter repositioning. The tensioning connector also serves to prevent inadvertent dislodging of the catheter's distal end anchor from the bronchus. In accordance with this embodiment the catheter includes at least one lumen through which the ventilation or therapeutic gas is delivered or insufflated directly into the targeted lung area and through which $CO_2$-rich mixed gas is removed or exhausted from the targeted area. Gas removal from the area is typically enhanced by applying vacuum, as opposed to passive exhaust, however a low vacuum level is applied to avoid the collapse of airways and trapping gas behind the then collapsed airways. Optionally the segmental ventilation gas delivery/removal cycle is synchronized with the breathing pattern of the complete lung either during natural breathing or during mechanical ventilation but can also be asynchronous. The primary segmental ventilation parameters, flow, pressure and frequency, are regulated so as to create the desired volume delivery to the targeted area, or alternatively the desired pressure delivery to and in the targeted area, or still alternatively the desired gas composition in the targeted area or perfusion network thereof. The segmental ventilation parameters are measured to facilitate such regulation and to maintain safe conditions such as to prevent barotrauma.

Still in accordance with the preferred embodiment of the present invention, the fluid delivered to the targeted area may include standard breathing gases such as filtered air-oxygen mixtures, or may include therapeutic gases, such as helium, helium-oxygen mixtures, nitric oxide, other low molecular weight gases and gases enriched with particalized medicants, or may include liquids such as perfluorocarbons. Hereafter, the various fluids potentially used in TTSV will be referred to as simply 'ventilation gas'.

Still in accordance with the preferred embodiment of the present invention, the proximal end of the catheter is kept external to the patient and is connected to a segmental ventilation gas control unit. The gas control unit comprises a supply of ventilation gas, or alternately an input connection means to a supply thereof, and comprises the requisite valves, pumps, regulators, conduits, sensors and control electronics to control the desired pressure and/or flow delivery of the gas and to control the desired pressure in the lung area. The gas control unit may comprise a replaceable or refillable modular cartridge of compressed or concentrated ventilation gas and/or may comprise a pump system that receives ventilation gas from a reservoir and ejects the ventilation gas into the catheter at the desired parameters. The gas control unit further comprises fail-safe over-pressure relief mechanisms to protect against inadvertent lung barotrauma. The gas control unit also typically comprises a negative pressure generating source and control system also connectable to a lumen in the catheter for the previously described gas removal phase, i.e., exhaust phase, of the gas control unit ventilation cycle. The gas control unit may be configured to be remove-ably or permanently attached internally or externally to a standard lung ventilator, in the case of performing gas control unit on a mechanically ventilated patient, or may be an independent unit optionally to be worn by an ambulatory patient, in the case of performing TTSV on for example a home-based naturally breathing patient. It is appreciated that the gas control unit will have the requisite control and monitoring interface to allow the user to control and monitor the relevant parameters of the TTSV, as well as the requisite power source, enclosure, electronics, etc.

In an optional embodiment of the present invention, an average pressure is created in the targeted lung area which is slightly elevated compared to the average pressure in the remainder of the lung. This is achieved by measuring and regulating the lung area and TTSV parameters accordingly. The purpose of the elevated pressure is four fold: (1) it will facilitate a dilitation of the distal airways to facilitate communication of the ventilation gas with the otherwise poorly communicating lung lobules and alveoli; (2) it will facilitate $CO_2$ displacement out of the elevated pressure area into areas of lower pressure due to simple flow and pressure gradient laws; (3) it will facilitate displacement of $CO_2$-rich gas out of very distal areas through collateral channels at the alveolar and lobular level into neighboring lung areas; (4) it will increase the rate of ventilation gas diffusion across the alveolar surface into the blood due to higher gas partial pressures, obeying diffusivity laws and hemoglobin biochemistry laws. Conversely, the average pressure created in the targeted area can also be regulated to produce a slightly lower average pressure than the remainder of the lung, in order to facilitate volume reduction of the targeted hyperinflated area.

TTSV can be performed by delivering ventilation gas to the targeted area but without applying an active exhaust phase as opposed to the previously described active exhaust phase. Or, alternatively, active insufflation and expiratory phases can simultaneously co-exist, rather than alternating between phases. Still alternately gas delivery and active gas exhaust can be continuous or semi-continuous rather than alternating with discrete phases of off and on. In any case, insufflation gas pressure and flow can be delivered continuously, variably, intermittently at low frequency, <20 cycles/min., intermittently at medium frequency, 20-50 cycles/min., intermittently at high frequency, >50 cycles/min., or synchronized with the patient's breathing cycle in order optimize the airflow fluid dynamics of TTSV. In the case of non-active expiration, the $CO_2$-rich gas is simply displaced by the insufflation gas and exits the targeted lung area passively due to concentration and pressure gradients. It can be appreciated that the possible combinations of pressure amplitudes and frequency profiles of both delivered and exhausted gases are extensive, but all must comply with the following fundamental and critical principle that is unique to the present invention: The regulated parameters must produce a decrease in stagnant gas in the treated area, produce an increase in beneficial gas in the treated area, avoid excessive or unsafe pressure and volume increases in the treated area, and ideally reduce the volume in the treated area to redistribute inspired air to other healthier lung areas.

In a second general embodiment of the present invention, regulation of the pressure in the ventilated segment is further facilitated by occluding the annular space between the catheter and the feeding bronchus of the ventilated segment. This embodiment further facilitates control of the pressure and gas concentration in the targeted lung area particularly in gravitationally challenging situations, for example when a non-gaseous substance is used in the ventilation fluid, or when a low molecular weight gas is used.

In a third general embodiment of the present invention, TTSV of targeted lung area is performed using gas removal only, rather than both gas delivery and gas removal. In this embodiment can be accomplished by applying, via the catheter, a vacuum to the area, or can be accomplished by creating a venturi effect by establishing a high velocity gas jet of positive pressure in the proximal direction to entrain gas out of the targeted lung area. The vacuum created by these later embodiments is typically very low level to avoid bronchial collapse, which may be determined by measuring gas flow and adjusting the vacuum level accordingly. Again, this form may be continuous, intermittent or variable and can be synchronized with the breathing cycle. It is understood that either form of gas evacuation will include the appropriate modifications to the gas control unit previously described.

In forth general embodiment of the present invention, a ventilation gas is delivered via the catheter into the targeted area for a desired period after which a vacuum is applied via the catheter to the bronchii feeding the targeted area also for a desired period. The vacuum amplitude is selected to collapse the bronchii thus trapping the ventilation gas in the area. Mixed gases are forced out during the ventilation gas delivery phase and also a portion of mixed gases are sucked out of the conducting airways immediately before their collapse at the beginning of the vacuum phase. The sequence is repeated successively until a predominant concentration of ventilation gas and minority of native gas occupies the area.

In a fifth general embodiment of the present invention, in order to improve ventilation in the lung as a whole, a segment which is not contributing much to gas exchange is blocked with an occlusive catheter to shunt inspired gas to other areas of the lung that are less diseased. Known as Trans-Tracheobronchial Segmental Shunting (TTSS), this embodiment can be useful considering that the more diseased less elastic areas preferentially fill with inspired air which does not reach the alveoli because of the large amount of stagnant trapped gas. TTSS can be performed continuously, semi-continuously, dynamically, or intermittently, or synchronized with the patients breathing cycle. TTSS can also be performed concurrently with some level of active gas removal using vacuum, and therapeutic gas or agent delivery into the blocked targeted area through the TTSS catheter. TTSS can also be performed with intermittent removal of the shunt but without removal of the catheter.

It should be noted that in some applications and embodiments of this invention, the TTSV or TTSS procedure is performed as a temporary palliative procedure with dramatic clinical benefit during the actual therapy but with a dissipating benefit after the therapy is discontinued. In other applications and embodiments, TTSV or TTSS is performed during mechanical ventilation to more effectively ventilate a patient, for example acutely to wean a patient from ventilatory support, or subchronically or chronically to improve ventilation in ventilatory-dependent patients. Still in other cases, TTSV or TTSS is performed on a naturally breathing patient as a chronic therapy either continuously or intermittently in order to provide clinical benefit lasting periods of weeks or even years. In this later embodiment, the catheter may be removed after a treatment while leaving a hygienic seal at the percutaneous access point, and a new catheter later inserted for a subsequent treatment. A guidewire might be left in place to ease subsequent re-catheterization. It should also be noted that the TTSV or TTSS procedure may be performed simultaneously on different lung areas or sequentially on the same or different lung areas. It should also be noted that TTSV or TTSS can be extremely useful for gradually reducing bulla in bullous emphysema, particularly if a stream of low molecular weight gas such as HeliOx is insufflated into the targeted lung area and mixed gases are removed with aspiration. Finally it should be noted that the TTSV or TTSS procedure can be performed on a relatively few large sections of lung, for example a lobe or a few lobar segments on patients with heterogeneous or bullous emphysema, or can be performed on many relatively small sections of lung, for example twelve sub-subsegments on patients with diffuse homogeneous emphysema. The procedure and treatment can even be performed on an entire lung by catheterizing a left or right mainstem bronchus, or both lungs by catheterizing the trachea.

As previously noted no methods exist in the prior art wherein a poorly functioning lung area with trapped $CO_2$-rich gas is more effectively ventilated by directly delivering ventilation gases to that area and/or removal of CO2-rich gas from that area, or of bronchial shunting of inspired air from a local lung area to other lung regions.

It should be noted that while preferred and optional embodiments of the present invention are described, there are other useful embodiments not specifically stated but are implied as part of the present invention which combine various features of the described embodiment.

BRIEF DESCRIPTION OF THE DRAWINGS

FIGS. 1 and 1A-1D describes the anatomy of a lung and placement of the TTSV catheter.

FIG. 3A-3E depicts TTSV therapy on a naturally breathing patient.

FIG. 4A-4C depicts TTSV therapy during mechanically ventilation.

FIG. 5 describes the effect of TTSV therapy on a naturally breathing patient.

FIG. 9A-9B describes typical TTSS catheters.

FIG. 10A-10K describes optional TTSV and TTSS catheter configurations.

FIG. 11 describes an over-guidewire and exchange catheter configuration.

FIG. 12A-12C describes means to allow the TTSV catheter to remain in place without irritating the bronchial walls.

DETAILED DESCRIPTION OF THE INVENTION

Figure 2A:
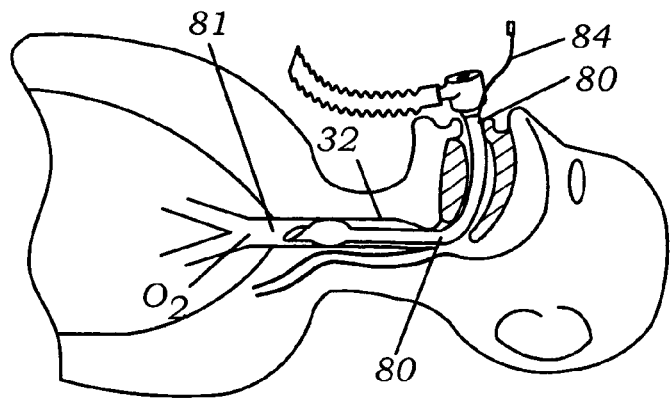
FIG. 2A-2C describes conventional ventilation therapies for treating compromised lungs.

Referring to FIG. 1 the lung anatomy is described including the left 30 and right 31 lung, trachea 32, the left main stem bronchus 33, the five lung lobes 36, 37, 38, 39, 40, a lateral fissure 41 separating the left upper and lower lobe, and the diaphragm 42 which is displaced downward indicative of a hyperinflated emphysematous lung. FIG. 1a shows a cut away view of the left upper lobe bronchus 43, the apical segmental bronchus 44 of the left upper lobe, the parietal pleura 45, the visceral pleura 46 and the pleural cavity 47. Large bulla 48 are membranous air vesicles created on the surface of the lung between the visceral pleura 46 and lung parenchyma 51 due to leakage of air out of the damaged distal airways and through the lung parenchyma. The air in the bullae is highly stagnant and does not easily communicate with the conducting airways making it very difficult to collapse bullae. Pleural adhesions 49 are fibrous tissue between the visceral pleura 46 and the parietal pleura 45 which arise from trauma or tissue fragility. These adhesions render it difficult to acutely deflate an emphysematous hyperinflated lung compartment without causing tissue injury such as tearing, hemorrhage or pneumothorax. FIG. 1b shows an exploded view of the upper lobe apical segment 52 and the anterior segment 54. FIG. 1d describes a non-emphysematous lung lobule which includes the functional units of gas exchange, the alveoli 55, and CO2-rich exhaled gas 58 easily exiting the respiratory bronchiole 56, Also shown are intersegmental collateral channels 57, typically 40-200 um in diameter, which communicate between bronchopulmonary segments making it difficult for a lung compartment to collapse or remain collapsed because of re-supply of air from neighboring compartments through these collateral channels. Detail C in FIG. 1c describes an emphysematous lung lobule in which the alveolar walls are destroyed from elastin breakdown resulting in large air sacks 59. The emphysematous lobule traps air becoming further hyperinflated because the respiratory bronchiole leading to the engorged lobule collapses 60 during exhalation, thus allowing air in but limiting air flow out 61.

FIG. 1 also shows the TTSV catheter 170 anchored in the apical segment bronchus 44. In FIG. 1b, the TTSV ventilation gas 71 is shown being delivered by the TTSV catheter 170. The native gas 72 in the targeted apical segment is forced out of the apical segment 52 proximally alongside the catheter 170 and also across intersegmental collateral channels into the neighboring anterior segment 54 then proximally up the airways. The native gas may also be sucked proximally up the catheter. The TTSV parameters are regulated to produce the desired pressure, volumes and gas concentrations.

Figure 2B:
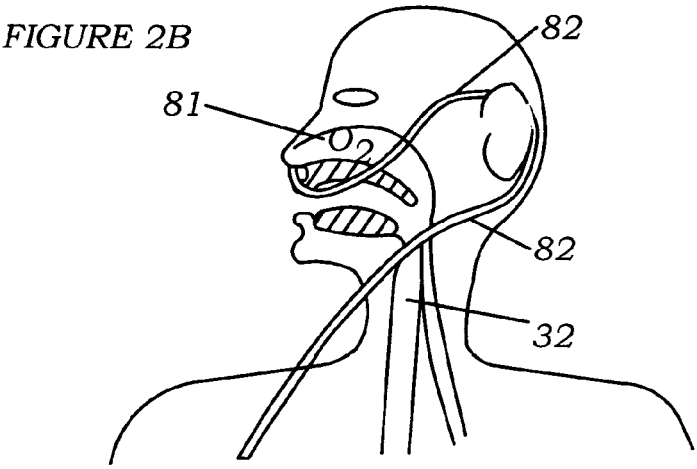
Figure 2C:
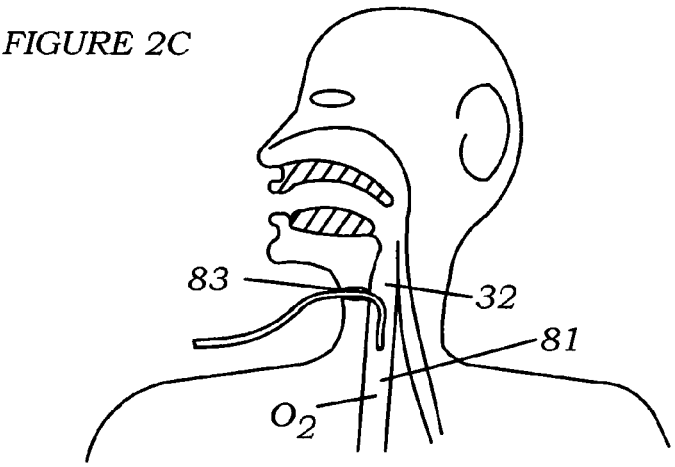

In FIG. 2 conventional therapies are shown which enhance gas exchange of a compromised lung. FIG. 2a shows mechanical ventilation in conjunction with Transtracheal Gas Insuflation (TGI) using an EndoTracheal Tube 80. Positive pressure is delivered to the lung via a mechanical ventilator and EndoTracheal Tube and the trachea 32 is insufflated with oxygen 81 via a dedicated lumen 84 in the EndoTracheal Tube to flush out retained CO2 in the trachea. This therapy does not address the stagnant gas in the hyperinflated lung areas that compromise ventilation. FIG. 2b shows long term oxygen therapy (LTOT) where oxygen 81 is delivered via nasal cannula 82. Again, while increasing O2 levels in the lung's upper airways, this therapy does not address the stagnant gas in the hyperinflated lung areas that compromise ventilation. FIG. 2c shows transtracheal oxygen therapy (TTOT) wherein oxygen 81 is delivered directly into the trachea 32 via a tracheotomy 83. While slightly more effective than LTOT, TTOT still has the same inherent shortcomings noted.

FIG. 3 describes a general layout of the invention disclosed herein, wherein TTSV or TTSS is performed on an ambulatory spontaneously breathing patient, showing percutaneous access into the trachea 32, catheterization of the targeted lung area 100, distal end anchoring 101, entry of the catheter 170 either nasally 102 or through a percutaneous incision 103, connection of the proximal end of the catheter to the wearable portable Gas Control Unit 104, in the case of TTSV therapy. Referring to FIG. 3b a cross-sectional view is shown of entry of the catheter into the patient showing a percutaneous connector 105 with a through-port and hygienic seal 106 and a securing means 107 fastening the seal to the neck of the patient. The hygienic seal 106 also prevents inadvertent unwanted axial movement of the catheter but allows desired axial sliding of the catheter in response to anticipated patient movement. The seal can be left in place to temporarily seal the incision with a self-sealing membrane or by attaching a plug 108 if the catheter is removed for extended periods.

FIG. 4 describes a general layout of the invention, wherein TTSV or TTSS is performed on a ventilatory dependent patient, showing entry of the catheter 170 through an endotracheal tube 120 which is in the trachea 32 of the patient, catheterization of the targeted lung area 121, connection of the proximal end of the catheter 122 to the ventilation Gas Control Unit 123, in the case of TTSV, as well as the ventilator 124 and breathing circuit 125. It can be seen that the catheter distal end is anchored 126 in the targeted bronchus and the catheter shaft at the patient entry point near the elbow connector 127 is tensioned 128 to prevent inadvertent unwanted movement with a tensioning and/or sealing means.

Figure 6:
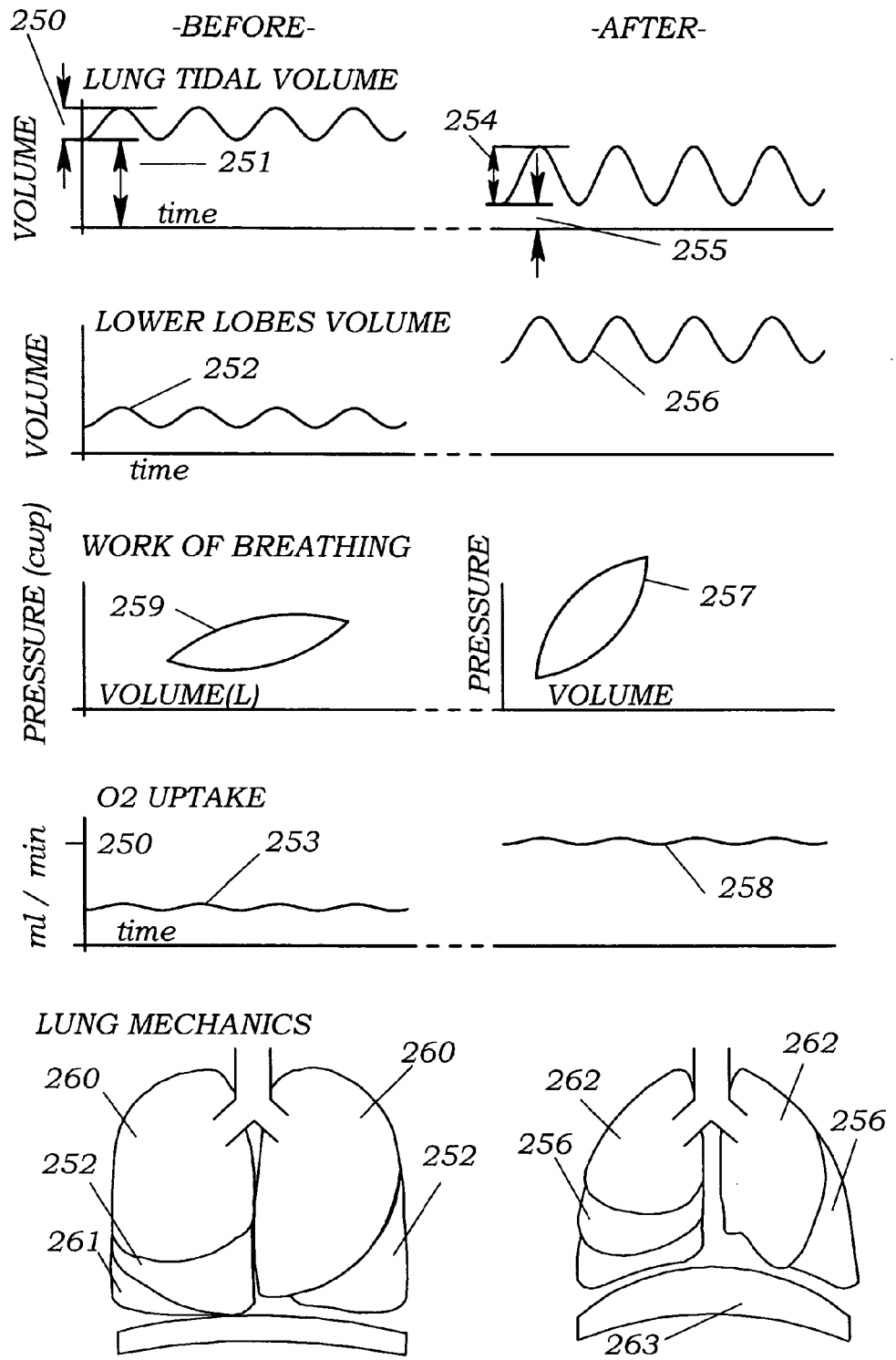
FIG. 6 describes the effect of TTSV therapy on a mechanically ventilated patient.
Figure 7A:
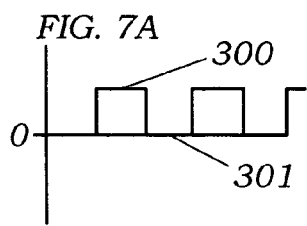
FIG. 7A-7Q describes optional TTSV treatment parameters.
Figure 7B:
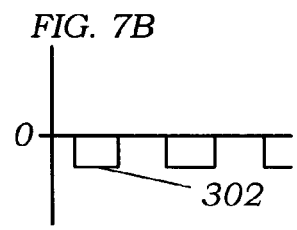
Figure 7C:
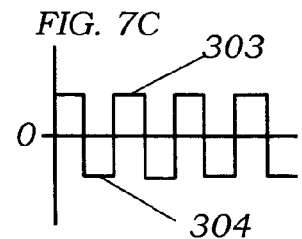
Figure 7D:
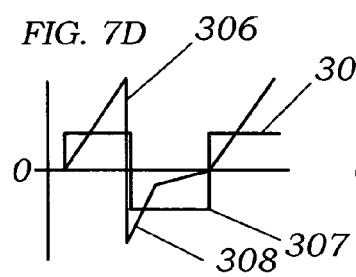
Figure 7E:
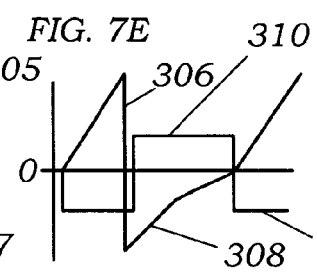
Figure 7F:
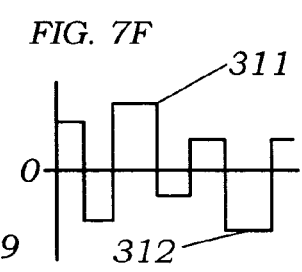
Figure 7G:
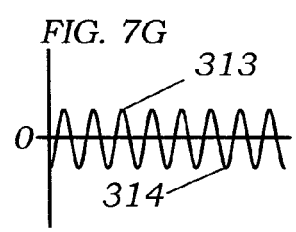
Figure 7H:
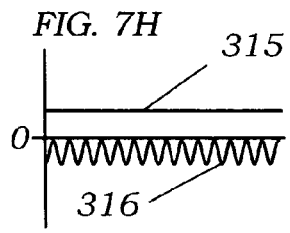
Figure 7I:
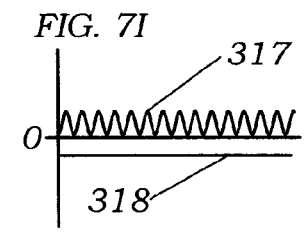
Figure 7J:
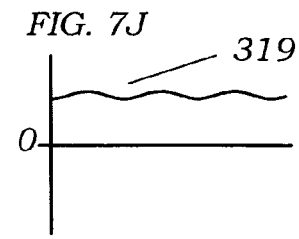
Figure 7K:
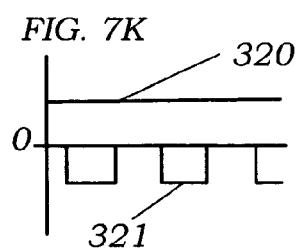
Figure 7L:
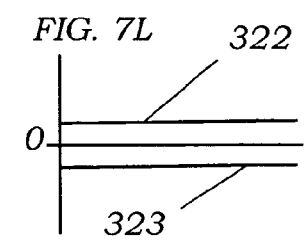
Figure 7M:
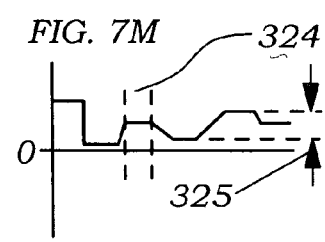
Figure 7N:
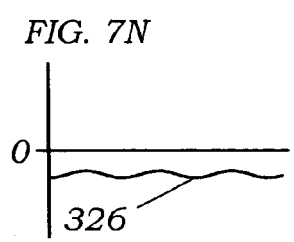
Figure 7O:
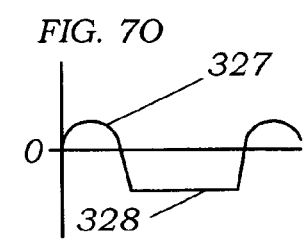

FIG. 5 graphically describes the effect of TTSV therapy performed on a naturally breathing patient. At baseline conditions the targeted lung area has an elevated gas volume 200 and the total lung has a tidal volume 201 with elevated residual volume 202. Due to gas trapping the targeted area has a predominant concentration of CO2-rich 203 stagnant gas with very little fresh CO2 coming from the blood stream, low blood perfusion due to shunting of blood to other lung areas, known as the Euhler reflex, and low O2 uptake 204. Work of breathing pressure-volume curves 212 of a breath indicate gas trapping and labored inspiration and exhalation. Breath air flow indicates a protracted exhalation 213 due to the poor lung elastic recoil. The lung itself has hyperinflated upper lobes 214 and diaphragm displaced downward 215. TTSV is commenced 205 by site-specific ventilation 206 of the targeted area, typically using 100% Oxygen or HeliOx or some other therapeutic gas delivered through the indwelling TTSV catheter. After therapeutic equilibrium, the targeted area gas volume is decreased 207, the native stagnant gas concentration in the targeted area is reduced dramatically 208 and is replaced by a high concentration of therapeutic gas 209 and fresh CO2 from the blood stream 210. Further, total lung residual volume decreases towards normal 211, O2 transfer increases 209 towards the normal value of 250 ml/min, work of breathing is less labored 216 and exhalation flow rate returns quickly to zero 217 due to improved recoil. The lung itself is less hyperinflated 218 and the diaphragm position returns toward normal 219. Depending on the parameters selected and other clinical factors, the therapeutic conditions can reach equilibrium in 30 minutes to 72 hours FIG. 6 graphically describes the effect of TTSS therapy performed on a mechanically ventilated patient. At baseline conditions the tidal volume in the lung 250 shows an elevated residual volume 251 and the volume in the lower lobes is abnormally low 252. Work of breathing shows poor or high lung compliance 259 in ml/cmH2O, and the overall gas exchange is comprised 253. The lung itself is hyperinflated, especially the upper lobes 260 and the diaphragm is displaced downward 261. After commencement of TTSS therapy the conditions begin to change due to the blocking of the targeted area by the blocking catheter, and optionally enhanced by applying a slight vacuum to the blocked area via the catheter. Due to absorption of the gas in the blocked area, or dissipation of the gas out of collateral channels, or by slight vacuum applied via the catheter, the volume in the targeted area decreases as does the overall lung volume 254 and lung residual volume 255. Some inspired gas volume is now diverted to the lower lobes 256, the lung compliance now decreases to a more healthy or elastic level 257 as shown by the pressure-volume curve of a breath, gas transfer returns to a more normal level 258, and the lung itself is less hyperinflated 262 and the diaphragm returns to a more normal position 263. Equilibrium can be reached between 30 minutes and 72 hours, depending on the targeted area blocked and other clinical conditions.

FIG. 7 graphically describes optional TTSV ventilation parameters with the abscissa and vertical coordinates corresponding to time and TTSV catheter pressure. FIG. 7a shows intermittent gas delivery with on 300 and off 301 times. FIG. 7b shows intermittent gas removal 302 by suctioning. FIG. 7c shows alternating gas delivery 303 and gas suctioning 304. FIG. 7d shows alternating gas delivery and suctioning synchronized with the breath cycle so that TTSV gas delivery 305 occurs during the inspiratory phase 306 and TTSV gas removal 307 occurs during the expiratory phase 308. FIG. 7e shows TTSV gas removal 309 synchronized with inspiration 306 and TTSV gas delivery 310 synchronized with exhalation 308. FIG. 7f shows changing levels and periods of TTSV gas delivery 311 and gas suctioning 312 wherein the levels are changing in order to maintain the desired conditions in the targeted area. FIG. 7g shows high frequency oscillatory gas delivery 313 and gas suctioning 314. FIG. 7h shows constant or static gas delivery 315 concurrent with high frequency oscillatory gas suctioning 316. FIG. 7i shows high frequency oscillatory gas delivery 317 concurrent with constant or static gas suctioning 318. FIG. 7j shows constant gas delivery 319 without any gas suctioning. FIG. 7k shows constant gas delivery 320 concurrent with intermittent gas suctioning 321. FIG. 7l shows concurrent constant gas delivery 322 and gas suctioning 323. FIG. 7m shows variable gas delivery periods 324 and amplitudes 325 in order to regulate the desired conditions in the targeted area. FIG. 7n shows constant or static vacuum 326 applied to the targeted lung area with out any gas delivery. FIG. 7o shows alternating gas delivery and gas suctioning with a short delivery phase 327 and extended vacuum phase 328.

Typical gas delivery and gas suction parameters depend on the area being treated and the clinical conditions. During mechanical ventilation, gas delivery can range from 0.1 to 1.5 lpm and 8 to 40 cmH2O at the lobar segment level and 1.0 to 10.0 lpm and 10 to 50 cmH2O at the tracheal level. Gas evacuation can range from 0.1 to 1.5 lpm and −5 to −40 cmH2O at the lobar segment level and 1.0 to 10.0 lpm and −10 to −50 cmH2O at the tracheal level. During spontaneous ventilation, flow can range from 0.05 to 1.5 lpm and 3 to 20 cmH2O at the lobar segment level and 1.0 to 10.0 lpm and 5 to 30 cmH2O at the tracheal level. Gas evacuation can range from 0.05 to 1.5 lpm and −3 to −20 cmH2O at the lobar segment level and 1.0 to 10.0 lpm and −5 to −30 cmH2O at the tracheal level. Frequencies can range from 1 to 120 cycles per hour if being used intermittently, and 2 to 120 cycles per minute in oscillatory mode, and 1 hour to indefinite durations for continuous mode.

Figure 8:
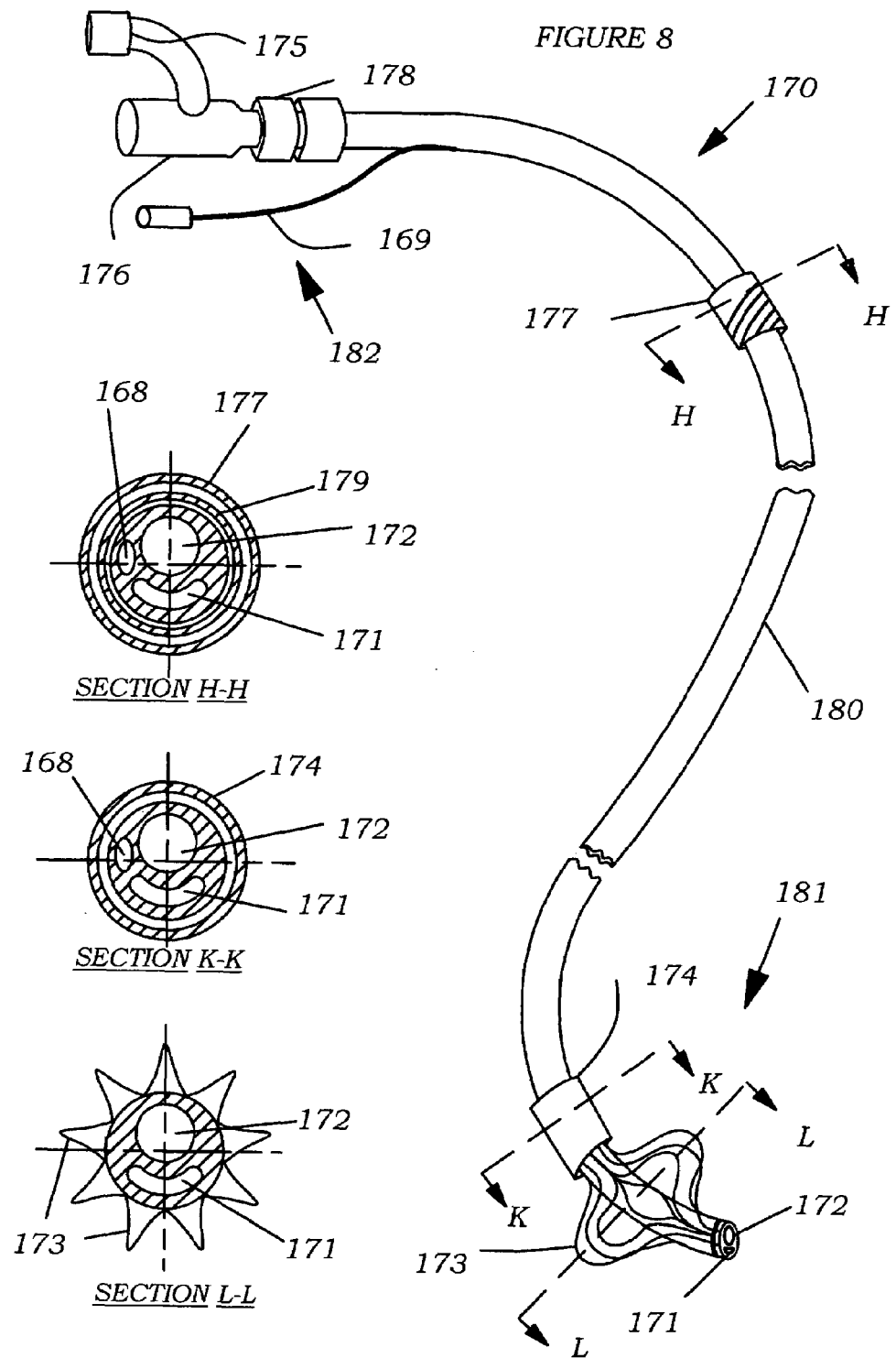
FIG. 8 describes a typical TTSV catheter.

FIG. 8 describes a typical TTSV catheter 170 with a catheter shaft 180 a distal end 181, a proximal end 182, a proximal end connector 176 for attachment to the TTSV Gas Control Unit, connection ports for insufflation flow 175 and suction 176, a distal end anchoring member 173, a slide-able sleeve 177 for placement in the percutaneous incision with a self-sealing gasket 179, a connection 178 for detachment of the proximal end of the catheter, a sleeve 174 for compressing the anchoring member 173, a mechanism 169 for retracting the sleeve 174, a lumen 168 for the mechanism 169, a lumen for gas delivery 171 and a lumen for gas suctioning 172.

FIG. 9 describes typical TTSS catheter configurations. FIG. 9a shows a dual TTSS catheter device, each catheter comprising a shaft 150, a balloon 151, for sealing at the distal tip of the catheter, a connector at the proximal end 152 of the catheter for optional connection to a suction source, a port 153 for inflation of the balloon, a through lumen 154 throughout the length of the catheter for guidewire insertion or for applying suction through the catheter, a 15 mm swivel elbow connector 155 for attachment to an endotracheal tube 156 and breathing circuit 157 and a port 158 for insertion of a bronchoscope if needed.

FIG. 9b shows a dual TTSS catheter integrated into the construction of an endotracheal tube 160. The TTSS catheters are slide-able within lumens 161 and 162 in the wall of the endotracheal tube. The catheters include connectors 163 for inflation of the occlusion balloons 164.

FIG. 10 describes alternate TTSV or TTSS catheter systems, devices and configurations. FIG. 10a shows a catheter with a self expanding woven wire anchor 400 which expands upon retraction of an outer sleeve 401 concentric to the catheter shaft 402. The catheter includes lumens for gas delivery 403 and gas removal 404. FIG. 10b shows a catheter with an inflatable balloon 405 which serves as an anchor and a bronchial occluder. The balloon is either electively inflatable, or is normally inflated and electively deflatable. FIG. 10c describes an inflatable anchor 407 in the shape of radial spokes 408 and hence anchors the catheter tip but does not occlude the bronchus. FIG. 10d describes a catheter with both an occlusive balloon 410 and a non-occlusive anchor 411. FIG. 10e shows a catheter with an inflatable balloon anchor 414 and in which the catheter includes a large port 415 communicating with a lumen 416 such that the anchor does not occlude the bronchus. Gas is free to flow between the treated area 417 and the proximal areas 418 to avoid the clinical problems of complete bronchial obstruction. FIG. 10f describes a catheter anchor comprised of wire loops 420. FIG. 10g describes a catheter with multiple small lumens 422 for gas delivery and a large lumen for gas suctioning 423. FIG. 10h shows a dual lumen catheter comprised of two concentric tubes 425 and 426 forming an inner lumen 427 and annular lumen 428, wherein the inner tube or lumen is recessed from the catheter tip. Suctioning is conducted through the annular lumen and gas delivery through the inner lumen such that the gas delivery can prevent clogging of the suctioning path by flushing out any debris 429. FIG. 10i describes a tri-lumen catheter with a lumen 432 for passage of a guidewire 433 wherein the guidewire may comprise a compressible anchoring feature 434 that can be retracted into the catheter lumen. FIG. 10j shows a dual lumen catheter in which the tip has been shaped to bend one lumen 440 180° such that the end of the lumen 441 points proximally away from the targeted lung area 442. Positive pressure is applied to the proximal end of this lumen to create a high velocity jet 443 at the distal port 441. The jet entrains gas in the targeted area 444 to be sucked out with the jet due to the venturi effect and thus allows for suctioning of gas but without the risk of clogging the catheter with debris. FIG. 10k describes another venturi system in which the tip of the catheter is configured such that positive pressure gas ports 450 are pointed proximally. High velocity gas exiting these ports 451 entrain gas in the targeted area 452 to be sucked out with the jet. These venturi configurations are especially useful in applications where gas removal is critical to the therapy and where there is a risk of catheter clogging if vacuum where to be used.

FIG. 11 describes a catheter exchange system wherein the catheter is placed over a guidewire and can be disconnected. The proximal section 480 or machine end which remains external to the patient, includes a connector 481 for connection to a TTSV ventilation control unit and a connector 482 for removal of the proximal section from the distal section 483. The distal section 483 or patient end which is predominantly inside the body, includes a receiving connector 485 for the proximal end and a slide-able sleeve 486 for placement in the percutaneous incision. The sleeve self-seals on the shaft of the catheter 487 and applies a slight amount of tension to the catheter shaft to prevent inadvertent dislodgement of the catheter from the lung. The sleeve also includes widenings 488 on both ends to anchor it in place on both sides of the incision. The distal section of the catheter also includes a stretchable section of catheter tubing 489 such that during movements of the patient's neck, the catheter length can change without transferring undesired tension to the distal end and inadvertently dislodging the catheter. Also included is a guidewire 490 that can be inserted and removed from a lumen 491 in the catheter, in order to initially place the catheter into the targeted site, or to place in the targeted site while the catheter is being removed, for example for cleaning or replacement.

Typical diameters of the TTSV catheter depend on the lung area being targeted. Some exemplary dimensions follow: Lobar segment: OD=2.0-3.5 mm; Lobar subsegment: OD=1.5-2.5 mm; Lobar sub-subsegment: OD=0.5-1.0 mm. TTSV catheter gas insufflation lumen diameters are typically 0.25-1.0 mm and gas exhaust lumens, if separately present, are typically comprise an area of 0.8-4.0 $mm^2$, preferably greater than 2.0 $mm^2$ to avoid mucous plugging. Catheter lengths are typically 120-150 cm. Anchoring forces are typically 1-10 psi and occlusion forces, if occlusion is utilized, are typically 0.2-0.5 psi. Anchors and occlusive member diameters depend on the targeted bronchial level and are up to 25 mm for main stem bronchus cannulation, 20 mm for lobar bronchus cannulation, 12 mm for segmental bronchi and 3 mm for sub-subsegmental bronchi cannulation when fully expanded. Proximal entry point tensioning forces typically produce 0.5-1.5 lbs of axial tension. The percutaneous plug is typically a soft rubber or thermoset material such as silicone. Some examples of catheter materials are; the shaft extrusion typically comprised of a thermoplastic or thermoset material such as nylon, PVC, polyethylene, PEBAX or silicone; the non-occlusive anchor typically comprised of a stainless steel or Nitinol wire; the inflatable occlusive member comprised of a highly compliant plastisol, silicone or urethane; connectors typically comprised of PVC, polysulfone, polypropylene or acrylic.

FIG. 12 describes a method and apparatus to allow the indwelling TTSV or TTSS catheter to remain in place for extended periods without irritating the bronchial walls and optionally to prevent dislodgement of the catheter during movement of the neck. FIG. 12a describes compressible loops 496 attached to the catheter 170 which can secure the catheter in place at various places along the tracheal-bronchial tree. The loops also center the catheter so that the catheter does not rub against the trachea 32 or airway walls. FIGS. 12b and 12c describe a bifurcated woven sleeve 498 and cylindrical sleeve 499 to which the catheter 170 is attached to center the catheter in the trachea 32 and airways and to absorb any tension applied to the distal end of the catheter.

Figure 13:
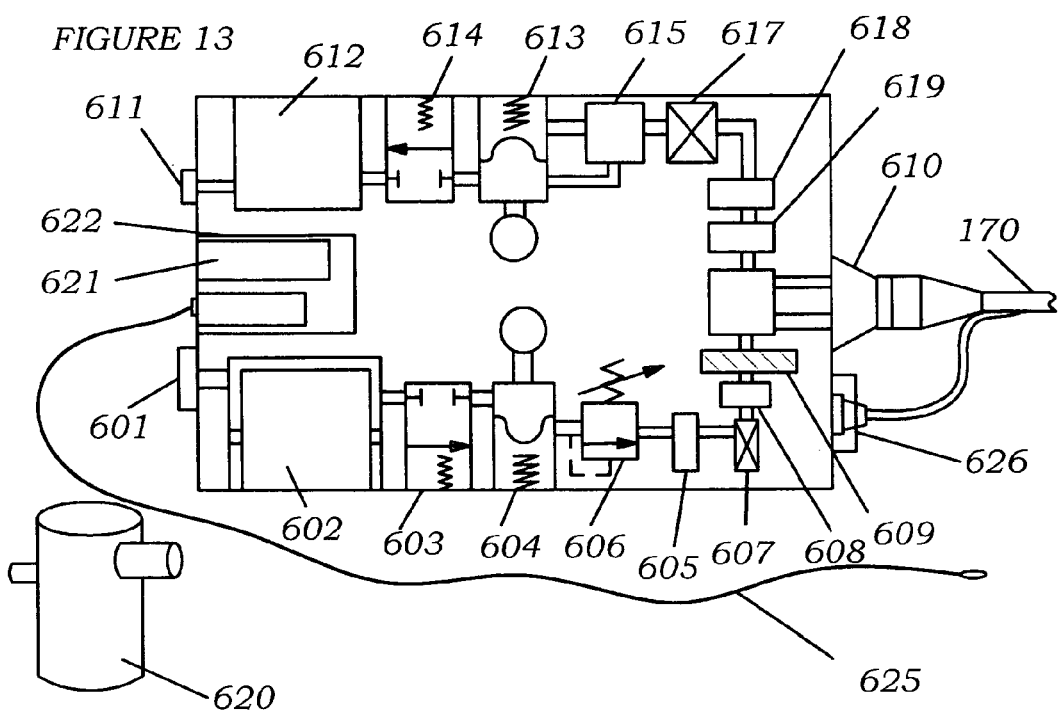
FIG. 13 describes the TTSV Gas Control Unit.

FIG. 13 describes the TTSV Gas Control Unit comprising both positive pressure gas delivery and negative pressure gas removal capability, although the unit may also comprise one or the other function. Shown on the insufflation side is a gas inlet connector 601 for a gas source, a gas reservoir or gas pressure pump 602, an insufflation pressure regulation valve 604, an on-off control valve 603, a pilot valve 605 for relaying a desired pressure reference to the pressure regulating valve with closed loop feedback control for proper pressure output, an over-pressure safety relief valve 606, a check valve 607, a pressure sensor 608, a gas outlet filter 609, and a TTSV catheter connector 610. Shown on the suction side is a vacuum source inlet connector 611, a vacuum reservoir or vacuum generation pump 612, a vacuum level regulation valve 613, an on-off control valve 614, vacuum pressure pilot pressure valve 615, a check valve 617, pressure sensor 618 and $CO_2$ sensor 619. A replaceable or refillable modular cartridge of ventilation gas 620 is shown as an alternative supply, typically housing 100-500 ml of compressed ventilation gas. For example a cartridge containing 250 ml of compressed gas pressurized at 10 psi would enable delivery of gas at a rate of 10 ml/hour at an average output pressure of 25 $cmH_2O$ for 20 days, based on ideal gas laws, and assuming 30% losses due to system leakage. Also shown is a power supply 621, and electrical circuitry 622 containing the signal processing, command center, microprocessor and imbedded software, a communication bus for inputs and outputs to and from the valves, sensors and user interface. An optional respiration sensor 625 is shown which controls or synchronizes the TTSV parameters if so desired. An optional control module 626 for controlling inflating and deflating the occlusive member at the distal tip of the catheter, if so equipped, is also shown. In other embodiments, the patient can use their own suction power generated by their lung for gas removal from the targeted area, for example by coupling their mouth to the proximal end of the catheter.

Figure 14:
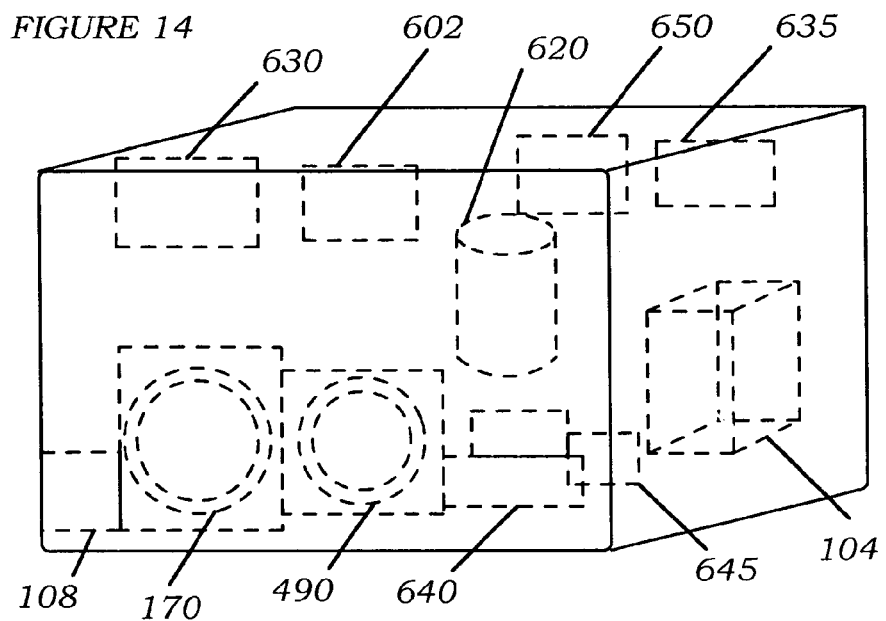
FIG. 14 describes a TTSV Kit.

FIG. 14 describes a kit including a sterile TTSV catheter assembly 170, a sterile guidewire 490, a percutaneous incision and dilitation kit 630, an access port plug 108, a Gas Control Unit 104, a gas cartridge 620, a holster for the Gas Control Unit 635, spare battery 602 and wall charger 640, cleaning supplies 645, instruction guide 650.

The invention claimed is:

1. A method of ventilating a patient, the method comprising:
    placing a percutaneous transtracheal ventilation catheter in an airway of the patient so that the catheter is anchored to allow extended use without vigilance and so that the patient's airway is patent to allow spontaneous breathing around the catheter;
    attaching the catheter to a ventilator external to the patient, wherein the ventilator is a wear-able ventilator; and
    ventilating the patient through the catheter by delivering gas at a positive pressure and flow rate sufficient to increase lung pressure.

2. An apparatus for ventilating a patient, the apparatus comprising:
    a ventilation catheter with a distal and proximal end, wherein the distal end is configured to be anchored in the patient's airway for extended use wherein the catheter does not occlude the airway, and wherein the proximal end is configured to be attached to an external ventilator, and comprising at least one lumen extending the length of the catheter, and
    a wear-able ventilator, comprising a gas delivery supply and a gas removal source coupled to the at least one lumen at the proximal end of the ventilation catheter, wherein the ventilator is configured to supply gas at a positive pressure and volumetric flow rate sufficient to increase lung pressure.

3. A method for directly ventilating a subject, comprising:
    placing a continuously indwelling catheter in a subject's bronchial tree beyond the lobar bronchus, wherein the catheter has a distal end and a proximal end, wherein the distal end is adapted to be anchored in the bronchus of the lung compartment, and wherein the catheter is adapted to remain in place for extended periods without clinician vigilance;

connecting the proximal end of the catheter to a wear-able ventilation source external to the patient, and wherein the ventilation source includes a gas removal source and a gas delivery supply, and wherein the catheter is configured to provide gas delivery and gas removal through the catheter; and ventilating the patient through the catheter by delivering gas at a positive pressure and rate sufficient to increase lung pressure.

4. A method for directly ventilating a patient using a wear-able ventilator, via an indwelling catheter placed in the patient's airway, the method comprising:

anchoring a distal end of the catheter within the patient's airway so that the catheter can remain in place for extended periods without vigilance;

connecting a proximal end of the catheter to a wear-able ventilator external to the patient, wherein the ventilator includes gas removal source and a gas delivery supply; and ventilating the patient through the catheter by delivering gas at a positive pressure and flow rate sufficient to increase lung pressure.

5. The method as in claim 4 wherein the step of ventilating comprises providing gas delivery and gas removal.

6. The method as in claim 5 wherein the gas delivery comprises applying pressure, wherein the pressure level is applied synchronous with the patient's breathing.

7. The method as in claim 4 wherein the step of ventilating comprises providing a gas delivery phase and a gas removal phase that alternate.

8. The method as in claim 4 wherein the step of ventilating comprises providing a gas delivery phase and a gas removal phase that alternate at a rate of one to sixty cycles per minute.

9. The method as in claim 4 wherein the step of ventilating comprises providing a gas delivery phase and a gas removal phase that are synchronized with a breath cycle.

10. The method as in claim 4 wherein the step of ventilating comprises providing a gas delivery phase and a gas removal phase that occur simultaneously.

11. The method as in claim 5 wherein parameters of the gas delivery and gas removal are controlled so that a residual volume in the lung area decreases.

12. The method as in claim 5 wherein the gas delivery comprises delivery of a ventilation gas and wherein the parameters of the gas delivery are regulated to obtain a predominant concentration of the ventilation gas in the target area.

13. The method as in claim 5 wherein the gas delivery comprises delivery of a ventilation gas to create an elevated pressure in a lung area for the purpose of facilitating displacement of stagnant native gas, mixed gases and waste gases from the area.

14. The method as in claim 5 wherein the step of ventilating comprises providing a pressure in a targeted area of the lung compartment by measuring pressure and adjusting the gas delivery and or the gas removal to achieve a desired pressure.

15. The method as in claim 5 wherein the step of ventilating comprises measuring a gas concentration in an area to determine completeness of native gas displacement from the area by the gas delivery and gas removal, or to determine and adjust parameters of the gas delivery and gas removal to optimize therapy.

16. The method as in claim 5 wherein the gas delivery and removal comprises positive pressure gas delivery, wherein the lung pressure is in the range of 3-20 cmH$_2$O and 8-40 cmH$_2$O during natural breathing and mechanical ventilation, respectively.

17. The method as in claim 5 wherein the gas delivery and removal comprises alternating positive pressure gas delivery to collapse bronchii feeding an area to trap delivered gas in the area.

18. The method as in claim 4 wherein the step of ventilating comprises providing gas flow rates of up to 10 lpm.

19. The method as in claim 4 wherein the airway feeding a targeted lung area remains patent during ventilation and is not occluded with the catheter.

20. The method as in claim 4 wherein the step of ventilating comprises providing passive gas exhaust from the area around the outside of the catheter.

21. The method as in claim 5 wherein the gas delivery is a therapeutic gas which is therapeutic to respiratory function selected from the group consisting of: 1000% O$_2$, Helium, HeliOx, Nitric Oxide, and combinations thereof.

22. The method as in claim 5 further comprising delivering a liquid that is therapeutic to the mechanics of respiration selected from the group consisting of:

Perfluorocarbon, surfactant, mucolytic, and combinations thereof.

23. The method as in claim 5 further comprising delivering a therapeutic substance to improve pulmonary function, selected from the group consisting of:

mucolytic agents, surfactants, beta-agonists, anti-inflammatories, steroids, antibiotics, vitamin derivatives, vasodilators, viral vector agents, mono-clonal antibodies, chemotherapeutics, radioactive isotopes, stem cells, and combinations thereof.

24. The method as in claim 4 wherein the step of ventilating the patient is performed concurrent with positive pressure ventilation from a mechanical ventilator, wherein the catheter is inserted into the patient's tracheobronchial tree through an artificial airway.

25. The method as in claim 4 wherein the step of ventilating the patient is performed on a naturally breathing patient, wherein the catheter is adapted to be inserted into the patient's tracheobronchial tree through a natural airway.

26. The method as in claim 4 further comprising ventilating different lung areas simultaneously or sequentially, wherein the lung areas include a bronchopulmonary compartment of the lung.

27. The method as in claim 4 wherein the procedure is adapted to be performed acutely for a period of 1-24 hours.

28. The method as in claim 4 further comprising guiding the catheter to a targeted lung area with a guiding member selected from the group consisting of: an endoscope, a fluoroscope, a guidewire or guiding catheter, an obturator, and combinations thereof.

29. The method as in claim 4 further comprising the step of pausing the step of ventilating and removing the catheter, wherein a guidewire is left in place to facilitate re-insertion of the catheter, and further comprising the steps of reinserting the catheter and resuming the ventilation.

30. The method as in claim 1, wherein the flow rate is set at a rate sufficient to achieve a desired volume output, wherein the desired volume output is sufficient to achieve a desired increase in lung pressure.

31. The method as in claim 1, wherein the step of ventilating the patient through the catheter comprises delivering gas at a flow rate of up to 10 lpm.

32. The device as in claim 2, wherein the wear-able ventilator is configured to supply gas at a gas flow rate of up to 10 lpm.

33. The method as in claim 4, wherein the step of anchoring the distal end of the catheter within the patient's airway comprises anchoring the distal end of the catheter within the subject's bronchial tree.

34. The method as in claim 4, wherein the flow rate is set at a rate sufficient to achieve a desired volume output, wherein the desired volume output is sufficient to achieve a desired increase in lung pressure.

35. The method as in claim 5, wherein the gas delivery comprises applying pressure wherein the pressure level is continuous.

36. The method as in claim 5, wherein the gas delivery comprises applying pressure wherein the pressure level is oscillatory.

37. The method as in claim 5, wherein the gas delivery and removal comprises positive pressure gas delivery, wherein the tracheal pressure is in the range of 5-30 cmH$_2$O and 10-50 cmH$_2$O during natural breathing and mechanical ventilation, respectively.

38. An apparatus for ventilating a patient, the apparatus comprising:
a percutaneous transtracheal ventilation catheter configured to be placed in an airway of the patient, wherein the catheter is configured to be anchored to allow extended use without vigilance and so that the patient's airway is patent to allow spontaneous breathing around the catheter;
a ventilator external to the patient, wherein the ventilator is a wear-able ventilator, and wherein the ventilator is configured to ventilate the patient through the catheter by delivering gas at a positive pressure and flow rate sufficient to increase lung pressure.

39. The apparatus as in claim 38, wherein the apparatus further comprises a vacuum source configured to suction $CO_2$ gas from the patient through the catheter.

40. The apparatus as in claim 38, wherein (i) the catheter comprises at least two lumens, (ii) the ventilator is configured to ventilate the patient through the catheter by delivering gas at a positive pressure and flow rate sufficient to increase lung pressure through the first lumen during an inspiration phase of the patient, and (iii) the ventilator is further configured to deliver gas through the second lumen to assist in the removal of $CO_2$-rich gas during an expiration phase of the patient.

41. The method as in claim 1, further comprising the step of assisting in removal of $CO_2$ gas from the patient.

42. The method as in claim 41, wherein the step of assisting in gas removal comprises using a vacuum source to suction $CO_2$ gas from the patient through the catheter.

43. The method as in claim 41, wherein (i) the catheter comprises at least two lumens, (ii) the step of ventilating the patient through the catheter by delivering gas at a positive pressure and flow rate sufficient to increase lung pressure comprises delivering the gas through the first lumen, and (iii) and the step of assisting in gas removal comprises delivering gas through the second lumen at a positive pressure and rate sufficient to assist in the removal of $CO_2$-rich gas during an expiration phase of the patient.

44. The apparatus as in claim 2 wherein the ventilation catheter is a percutaneous transtracheal catheter.

45. The apparatus as in claim 2 wherein the ventilation catheter passes through the nasal airway.

46. The apparatus as in claim 2 wherein the ventilation catheter further comprises a connector adapted to connect to a tracheal tube.

47. The apparatus as in claim 2 wherein the at least one lumen of the ventilation catheter comprises at least two lumens, wherein a first lumen is in communication with the gas removal source and a second lumen is in communication with the gas delivery supply.

48. The apparatus as in claim 2 wherein the ventilation catheter further comprises a connector external to the patient adapted to removably attach a portion of the catheter wholly external to the patient to a portion of the catheter partly internal to the patient.

49. The apparatus as in claim 2 wherein the ventilation catheter further comprises a sealing and tensioning connector adapted to seal and secure the catheter to a percutaneous access site.

50. The apparatus as in claim 2 wherein the ventilation catheter further comprises a sealing and tensioning connector adapted to seal and secure the catheter to a tracheal tube.

51. The apparatus as in claim 2 wherein the ventilation catheter has a length of 25-300 cm, an outer diameter of 1 to 5 mm, and a ventilation gas delivery lumen effective diameter of 0.1 to 3.0 mm.

52. The apparatus as in claim 47 wherein the effective diameter of the second lumen is 0.1 to 3.0 mm and the effective diameter of the first lumen is 0.3 to 1.0 mm.

53. The apparatus as in claim 2 wherein the ventilation catheter comprises an extruded thermoplastic or thermoset material of 30-70 Shore A durometer.

54. The apparatus as in claim 2 wherein the ventilation catheter comprises a therapeutic compound selected from the group consisting of an antibiotic coating, antimicrobial coating, and an antifungal coating.

55. The apparatus as in claim 2 wherein the ventilation catheter comprises a radiopaque constituent or radiopaque marking.

56. The apparatus as in claim 2 wherein the ventilation catheter comprises at least one section having circumferential ridges adapted to lengthen or shorten the catheter length and to absorb forces.

57. An apparatus for ventilating a patient, the apparatus comprising:
a ventilation catheter with a distal and proximal end, wherein the distal end is configured to be anchored in the patient's airway for extended use, wherein the catheter does not occlude the airway, and wherein the proximal end is configured to be attached to an external ventilator, and comprising at least one lumen extending the length of the catheter, and
a wear-able ventilator, comprising a gas delivery supply coupled to the at least one lumen at the proximal end of the ventilation catheter, wherein the ventilator is configured to supply gas at a positive pressure and volumetric flow rate sufficient to increase lung pressure during an inspiration phase of the patient and wherein the ventilator is configured to deliver gas through the second lumen to assist in the removal of $CO_2$-rich gas during an expiration phase of the patient.

58. The apparatus as in claim 57,
wherein the at least one lumen of the ventilation catheter comprises at least two lumens,
wherein a first lumen is adapted for gas delivery and comprises a first gas delivery port at the distal end of the catheter, wherein the first gas delivery port is oriented and adapted to direct gas being delivered by the first lumen toward the lung,
wherein a second lumen is adapted for gas delivery and comprises a second gas port near the distal end of the catheter, wherein the second gas port is oriented and adapted to direct gas being delivered by the second lumen away from the lung, wherein the ventilator is adapted to deliver ventilation gas through the first lumen during inspiration,
and wherein the ventilator is adapted to deliver gas through the second lumen during expiration.

59. The apparatus as in claim 2 wherein the ventilator further comprises a ventilation gas control unit in communication with a ventilation gas supply, wherein the ventilation gas control unit comprises pressure and flow measuring and regulating devices, and wherein the ventilation gas control unit is adapted to produce and regulate a desired pressure and flow output of the ventilator and a desired airway pressure.

60. The apparatus as in claim 59 wherein the desired airway pressure measured in the trachea is 5-30 cm $H_2O$.

61. The apparatus as in claim 59 wherein the ventilation gas control unit communicates with a vacuum source, and wherein the ventilation gas control unit further comprises at least one vacuum measuring and regulating device, and the ventilation gas control unit is further adapted to produce and regulate a desired vacuum level output of the ventilator and a desired airway pressure or gas composition.

62. The apparatus as in claim 2 wherein the ventilator further comprises an airway pressure measuring device, wherein airway pressure measurements are used to adjust the output of the ventilator.

63. The apparatus as in claim 2 wherein the ventilator further comprises an airway $CO_2$ measuring device wherein airway $CO_2$ is used to adjust the output of the ventilator.

64. The apparatus as in claim 2 wherein the ventilator further comprises a user interface, wherein the user interface is adapted to allow selection and display of desired ventilation parameters, and display of monitored ventilation parameters.

65. The apparatus as in claim 2 wherein the ventilator is a module of a mechanical ventilator.

66. The apparatus as in claim 2 wherein the gas delivery supply comprises an internal pressurized gas source, the gas removal source comprises an internal vacuum source, and the ventilator further comprises an internal battery and a fastener selected from the group consisting of a belt clip, a shoulder strap, and a pack.

67. The apparatus as in claim 2 wherein the ventilator further comprises an integral removable and replaceable ventilation gas supply container.

68. The apparatus as in claim 2 wherein the ventilator further comprises an integral refillable ventilation gas supply container.

69. The apparatus as in claim 2 wherein the ventilator is adapted to produce a tracheal airway pressure of 5-30 cm $H_2O$.

70. The apparatus as in claim 2 wherein the ventilator is adapted to produce a lobar segmental bronchus airway pressure of 3-20 cm $H_2O$.

71. The apparatus as in claim 2 wherein the ventilator is adapted to produce an airway pressure at the lung lobar segmental level of 3-20 cm $H_2O$.

72. The apparatus as in claim 2 wherein the catheter is adapted so the distal tip may be placed in the tracheal airway.

73. The apparatus as in claim 2 wherein the catheter is adapted to be placed through the nasal airway.

74. The apparatus as in claim 2 wherein the catheter is adapted so the distal tip may be placed in a main stem bronchus airway.

75. The apparatus as in claim 2 wherein the catheter is adapted so the distal tip may be placed in a lobar bronchus airway.

76. The apparatus as in claim 2 wherein the catheter is adapted so the distal tip may be placed in a segmental bronchus airway.

77. The method as in claim 4 wherein the step of ventilating the patient is performed on a naturally breathing patient, wherein the catheter is adapted to be inserted into the patient's tracheobronchial tree through an unnatural channel selected from the group consisting of: a cricothyrotomy, a tracheotomy, or combinations thereof.

78. The method as in claim 4 wherein the gas is delivered at a positive pressure and flow rate sufficient to produce a tracheal airway pressure in the range of 5-30 cm $H_2O$.

79. The method as in claim 4 wherein the gas is delivered at a positive pressure and flow rate sufficient to produce a lobar segmental bronchus airway pressure in the range of 3-20 cm $H_2O$.

80. The method as in claim 4 further comprising placing a distal tip of the catheter in the trachea.

81. The method as in claim 4 further comprising placing a distal tip of the catheter distal to the carina.

82. The method as in claim 4 further comprising placing a distal tip of the catheter in the lobar bronchus.

83. The method as in claim 4 further comprising placing a distal tip of the catheter distal to the lobar bronchus.

84. The method as in claim 4 wherein the catheter is connected to a tracheal tube.

85. The method as in claim 25 wherein the natural airway is the nasal airway.

86. A method for directly ventilating a patient via an indwelling catheter placed in the-patient's airway and using a wear-able ventilator, the method comprising:
anchoring a distal end of the catheter within the patient's airway so that the catheter can remain in place for extended periods without vigilance;
connecting a proximal end of the catheter to a wear-able ventilator external to the patient, wherein the ventilator includes a gas delivery supply; and
ventilating the patient through the catheter by (i) delivering gas at a positive pressure and rate sufficient to increase lung pressure during an inspiration phase of the patient and (ii) delivering gas at a positive pressure and rate sufficient to assist in the removal of $CO_2$-rich gas during an expiration phase of the patient.

87. The method as in claim 86,
wherein the catheter comprises at least two lumens;
wherein a first lumen is adapted for gas delivery and comprises a first gas delivery port at the distal end of the catheter, wherein the first gas delivery port is oriented and adapted to direct gas being delivered by the first lumen toward the lung;
wherein a second lumen is adapted for gas delivery and comprises a second gas port near the distal end of the catheter, wherein the second gas port is oriented and adapted to direct gas being delivered by the second lumen away from the lung;
wherein the ventilator is adapted to deliver ventilation gas through the first lumen during the inspiration phase of the patient;
and wherein the ventilator is adapted to deliver gas through the second lumen during the expiration phase of the patient.

* * * * *

UNITED STATES PATENT AND TRADEMARK OFFICE
CERTIFICATE OF CORRECTION

| | | |
|---|---|---|
| PATENT NO. | : 7,588,033 B2 | Page 1 of 1 |
| APPLICATION NO. | : 10/870849 | |
| DATED | : September 15, 2009 | |
| INVENTOR(S) | : Anthony David Wondka | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 652 days.

Signed and Sealed this

Twenty-first Day of September, 2010

David J. Kappos
*Director of the United States Patent and Trademark Office*